United States Patent
Tsukamoto et al.

(10) Patent No.: US 9,603,897 B2
(45) Date of Patent: Mar. 28, 2017

(54) METHODS FOR TREATING TISSUE DAMAGE ASSOCIATED WITH ISCHEMIA WITH APOLIPOPROTEIN D

(71) Applicant: Massachusetts Institute of Technology, Cambridge, MA (US)

(72) Inventors: Kosuke Tsukamoto, Osaka (JP); Monty Krieger, Needham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/377,750

(22) PCT Filed: Mar. 12, 2013

(86) PCT No.: PCT/US2013/030525
§ 371 (c)(1),
(2) Date: Aug. 8, 2014

(87) PCT Pub. No.: WO2013/138338
PCT Pub. Date: Sep. 19, 2013

(65) Prior Publication Data
US 2015/0352181 A1 Dec. 10, 2015

Related U.S. Application Data

(60) Provisional application No. 61/609,547, filed on Mar. 12, 2012.

(51) Int. Cl.
| C07K 14/775 | (2006.01) |
| A61K 38/17 | (2006.01) |
| A61K 45/06 | (2006.01) |
| C12N 7/00 | (2006.01) |
| C12N 15/86 | (2006.01) |

(52) U.S. Cl.
CPC .......... *A61K 38/1709* (2013.01); *A61K 45/06* (2013.01); *C12N 7/00* (2013.01); *C12N 15/86* (2013.01); *C12N 2710/10032* (2013.01); *C12N 2710/10041* (2013.01); *C12N 2740/15032* (2013.01); *C12N 2740/15041* (2013.01)

(58) Field of Classification Search
CPC .................................................. C07K 14/775
See application file for complete search history.

(56) References Cited

FOREIGN PATENT DOCUMENTS

WO 2005/084642 A1 9/2005

OTHER PUBLICATIONS

Thabut et al. 2007; High density lipoprotein administration attenuates liver proinflammatory response, restores liver endothelial nitric oxide synthase activity, and lowers portal pressure in cirrhotic rats. Hepatology. 46(6): 1893-1906.*
Lapergue et al. 2010; Protective effect of high-density lipoprotein-based therapy in a model of embolic stroke. Stroke 41: 1536-1542.*
Brewer (2009a; Update on the role of HDL infusions in the treatment of patients with cardiovascular disease. Atherosclerosis Supplement. 10(2); Abstract 1452.*
He et al. 2009; Apolipoprotein D moductes F2-isoprostane and 7-ketocholesterol formation and has a neuroprotective effect on organotypic hippocampal cultures after kainite-induced excitotoxic injury. Neuroscience Letters. 455: 183-186.*
Mayo Clinic 1998; Coronary Artery Disease. On the web at mayoclinic.org/diseases-conditions/coronary-artery-disease/diagnosis-treatment.*
International Preliminary Report on Patentability, PCT/US2013/030525, dated Sep. 16, 2014, 8 pages.
International Search Report and Written Opinion, PCT/US2013/030525, dated Oct. 16, 2013, 13 pages.
James, R.W. et al., "Apoprotein D in a Healthy, Male Population and in Male Myocardial Infarction Patients and Their Male, First-Degree Relatives," Atherosclerosis, vol. 60(1), pp. 49-53 (1986).
Lelden, J., "Adenovirus-mediated Gene Transfer as an In Vivo Probe of Lipoprotein Metabolism," Circulation, vol. 94(9), pp. 2046-2051 (1996).
Muffat, J. et al., "Apolipoprotein D: An overview of its role in aging and age-related diseases," Cell Cycle, vol. 9(2), pp. 269-273 (2010).
Perdomo, G. et al.: "Apolipoprotein D in lipid metabolism and its functional implication in atherosclerosis and aging," Aging, vol. 1(1), pp. 17-27 (2009).
Ruscher, K. et al., "Effects of Chronic Clozapine Administration on Apolipoprotein D levels and on functional recovery following experimental stroke," Brain Research, Elsevier, Amsterdam, vol. 1321, pp. 152-163 (2010).
Sarjeant, J., "Apolipoprotein D Inhibits Platelet-Derived Growth Factor-BB-Induced Vascular Smooth Muscle Cell Proliferated by Preventing Translocation of Phosphorylated Extracellular Signal Regulated Kinase ½ to the Nucleus," Arteriosclerosis, Thrombosis, and Vascular Biology, vol. 23(12), pp. 2172-2177 (2003).

* cited by examiner

*Primary Examiner* — Karen Cochrane Carlson
(74) *Attorney, Agent, or Firm* — Nelson Mullins Riley & Scarborough LLP; Amy E. Mandragouras, Esq.; Ariana D. Harris

(57) ABSTRACT

The invention provides methods for treating tissue damage associated with impaired blood flow using ApoD, or an active variant thereof, or an agent that increases the expression of ApoD. The invention also encompasses active variants of ApoD for use in the methods.

21 Claims, 7 Drawing Sheets

SEQUENCE LISTING

<160> NUMBER OF SEQ ID NOS: 9

<210> SEQ ID NO 1
<211> LENGTH: 169
<212> TYPE: PRT
<213> ORGANISM: Homo sapiens
<220> FEATURE:
<221> NAME/KEY: misc_feature
<223> OTHER INFORMATION: Human mature ApoD

<400> SEQUENCE: 1

Gln Ala Phe His Leu Gly Lys Cys Pro Asn Pro Pro Val Gln Glu Asn
1               5                   10                  15

Phe Asp Val Asn Lys Tyr Leu Gly Arg Trp Tyr Glu Ile Glu Lys Ile
            20                  25                  30

Pro Thr Thr Phe Glu Asn Gly Arg Cys Ile Gln Ala Asn Tyr Ser Leu
        35                  40                  45

Met Glu Asn Gly Lys Ile Lys Val Leu Asn Gln Glu Leu Arg Ala Asp
    50                  55                  60

Gly Thr Val Asn Gln Ile Glu Gly Glu Ala Thr Pro Val Asn Leu Thr
65                  70                  75                  80

Glu Pro Ala Lys Leu Glu Val Lys Phe Ser Trp Phe Met Pro Ser Ala
                85                  90                  95

```
Pro Tyr Trp Ile Leu Ala Thr Asp Tyr Glu Asn Tyr Ala Leu Val Tyr
            100                 105                 110

Ser Cys Thr Cys Ile Ile Gln Leu Phe His Val Asp Phe Ala Trp Ile
            115                 120                 125

Leu Ala Arg Asn Pro Asn Leu Pro Pro Glu Thr Val Asp Ser Leu Lys
            130                 135                 140

Asn Ile Leu Thr Ser Asn Asn Ile Asp Val Lys Lys Met Thr Val Thr
145                 150                 155                 160

Asp Gln Val Asn Cys Pro Lys Leu Ser
                165
```

<210> SEQ ID NO 2
<211> LENGTH: 507
<212> TYPE: DNA
<213> ORGANISM: Homo sapiens
<220> FEATURE:
<221> NAME/KEY: misc_feature
<223> OTHER INFORMATION: Human mature ApoD

<400> SEQUENCE: 2

```
caagcatttc atcttgggaa gtgccccaat cctccggtgc aggagaattt tgacgtgaat     60
aagtatctcg gaagatggta cgaaattgag aagatcccaa caacctttga aatggacgc    120
tgcatccagg ccaactactc actaatggaa acggaaaga tcaaagtgtt aaaccaggag    180
ttgagagctg atggaactgt gaatcaaatc gaaggtgaag ccaccccagt taaccctcaca  240
gagcctgcca agctggaagt taagtttttcc tggtttatgc catcggcacc gtactggatc  300
ctggccaccg actatgagaa ctatgccctc gtgtattcct gtacctgcat catccaactt   360
tttcacgtgg attttgcttg gatcttggca agaaacccta atctccctcc agaaacagtg   420
gactctctaa aaatatcct gacttctaat aacattgatg tcaagaaaat gacggtcaca    480
gaccaggtga actgccccaa gctctcg                                       507
```

<210> SEQ ID NO 3
<211> LENGTH: 189
<212> TYPE: PRT
<213> ORGANISM: Homo sapiens
<220> FEATURE:
<221> NAME/KEY: misc_feature
<223> OTHER INFORMATION: Human ApoD precursor

<400> SEQUENCE: 3

```
Met Val Met Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu
            35                  40                  45

Ile Glu Lys Ile Pro Thr Thr Phe Glu Asn Gly Arg Cys Ile Gln Ala
50                  55                  60

Asn Tyr Ser Leu Met Glu Asn Gly Lys Ile Lys Val Leu Asn Gln Glu
65                  70                  75                  80

Leu Arg Ala Asp Gly Thr Val Asn Gln Ile Glu Gly Glu Ala Thr Pro
            85                  90                  95

Val Asn Leu Thr Glu Pro Ala Lys Leu Glu Val Lys Phe Ser Trp Phe
            100                 105                 110

Met Pro Ser Ala Pro Tyr Trp Ile Leu Ala Thr Asp Tyr Glu Asn Tyr
            115                 120                 125
```

```
Ala Leu Val Tyr Ser Cys Thr Cys Ile Ile Gln Leu Phe His Val Asp
        130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser
                180                 185
```

```
<210> SEQ ID NO 4
<211> LENGTH: 567
<212> TYPE: DNA
<213> ORGANISM: Homo sapiens
<220> FEATURE:
<221> NAME/KEY: misc_feature
<223> OTHER INFORMATION: Human ApoD precursor

<400> SEQUENCE: 4
atggtgatgc tgctgctgct gctttccgca ctggctggcc tcttcggtgc ggcagaggga      60
caagcatttc atcttgggaa gtgccccaat cctccggtgc aggagaattt tgacgtgaat     120
aagtatctcg gaagatggta cgaaattgag aagatcccaa caacctttga gaatggacgc     180
tgcatccagg ccaactactc actaatggaa acggaaagaa tcaaagtgtt aaaccaggag     240
ttgagagctg atggaactgt gaatcaaatc gaaggtgaag ccaccccagt taacctcaca     300
gagcctgcca agctggaagt taagttttcc tggtttatgc catcggcacc gtactggatc     360
ctggccaccg actatgagaa ctatgccctc gtgtattcct gtacctgcat catccaactt     420
tttcacgtgg attttgcttg gatcttggca agaaacccta atctccctcc agaaacagtg     480
gactctctaa aaatatcct gacttctaat aacattgatg tcaagaaaat gacggtcaca     540
gaccaggtga actgccccaa gctctcg                                         567
```

```
<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
aatgcaatcc tgattctgct t                                                21
```

```
<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
gctcagagcc ttgatacc                                                    18
```

```
<210> SEQ ID NO 7
<211> LENGTH: 25
<212> TYPE: DNA
<213> ORGANISM: Artificial Sequence
<220> FEATURE:
<223> OTHER INFORMATION: Synthetic primer

<400> SEQUENCE: 7
aagttggacc tacacatcag ctgac                                            25
```

```
<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
tgcgaggcca gaggccactt gtgtagc                                         27

<210> SEQ ID NO 9
<211> LENGTH: 27
<212> TYPE: DNA
<213> ORGANISM: Artificial Sequence
<220> FEATURE:
<223> OTHER INFORMATION: Synthetic primer

<400> SEQUENCE: 9 cttttcacg tcaaaattct cttgcac                                          27
```

METHODS FOR TREATING TISSUE DAMAGE ASSOCIATED WITH ISCHEMIA WITH APOLIPOPROTEIN D

CROSS-REFERENCE TO RELATED APPLICATIONS

This application is a 35 U.S.C. 371 national stage filing of International Application PCT/US2013/030525, filed Mar. 12, 2013, which claims priority to U.S. Provisional Patent Application 61/609,547 filed Mar. 12, 2012. The contents of the aforementioned applications are hereby incorporated by reference herein in their entirety.

STATEMENT REGARDING SEQUENCE LISTING

The instant application contains a Sequence Listing which has been submitted electronically in ASCII format and is hereby incorporated by reference in its entirety. Said ASCII copy, created on Aug. 8, 2014, is named MITN_023US_Sequence_Listing.txt and is 6423 Kilobytes in size. The Sequence Listing is being submitted by EFS Web and is hereby incorporated by reference into the specification.

BACKGROUND OF THE INVENTION

Apolipoprotein D ("ApoD") is a 169 residue, 29 kDa glycoprotein member of the lipocalcin family that binds to several ligands, including progesterone and arachidonic acid, and is associated with HDL in plasma. It is highly expressed in nervous tissue (e.g., brain in glia and neurons) and apparently at lower levels in many other tissues under normal conditions. ApoD expression increases with aging and in neurological and psychiatric disorders (e.g., Alzheimer's Disease, Parkinson's Disease, Schizophrenia, bipolar disorder, and by the antipsychotic clozapine, and in some cancers). While ApoD has been widely used as a disease marker, little is known about its potential therapeutic effects.

Tissue damage can result from an imbalance between oxygen supply and demand in tissue, i.e., ischemia. For instance, myocardial ischemia is a pathological state associated with coronary artery disease that results from reduced blood perfusion in the heart, leading to impaired oxygen supply to the heart. Current interventions for improving blood flow to damaged heart tissue are mostly invasive, including stent placement, coronary bypass surgery, angioplasty, and endarterectomy. The high risk associated with these invasive procedures underscores the need for additional therapies and therapeutic agents for treating or reducing tissue damage resulting from ischemia, for example, myocardial ischemia.

SUMMARY OF THE INVENTION

The present invention is based, in part, on the discovery that tissue damage resulting from ischemia and ischemia/reperfusion stress, such as cardiac tissue damage, can be treated by administering a prophylactic or therapeutic amount of ApoD. Treatment occurs even when the source of the ApoD is generalized, such as, for example by production in the liver following injection of ApoD expressing virus, indicating that circulating ApoD results in a tissue- or cardio-protective effect. The protective role of ApoD is further indicated by the exacerbation of cardiac tissue damage in ApoD knockout mice in response to ischemia/reperfusion, and evidenced by the ability of ApoD to protect cardiomyocytes from hypoxic stress.

The present invention, in general, relates to methods of reducing or treating tissue damage resulting from impaired blood flow by administering an effective amount of ApoD, or an active variant thereof, or an agent that increases the expression of ApoD, to reduce the tissue damage.

Accordingly, in one aspect, the invention relates to the treatment of ischemic injury or ischemia/reperfusion injury in a tissue by administering to a subject a composition including an effective amount of ApoD, or an active variant thereof, or an agent that increases the expression of ApoD, to thereby treat ischemic injury or ischemia/reperfusion injury in the tissue.

In another aspect, the invention relates to treating a subject at risk of tissue damage associated with ischemia or ischemia/reperfusion, by administering to a subject a composition including an effective amount of ApoD, or an active variant thereof, or an agent that increases the expression of ApoD, to thereby treat the subject at risk of tissue damage.

In another aspect, the invention relates to treating tissue damage associated with myocardial infarction or coronary artery disease, by administering to a subject a composition including an effective amount of ApoD, or an active variant thereof, or an agent that increases the expression of ApoD, to thereby treat tissue damage in the subject.

In another aspect, the invention relates to treating a subject at risk of tissue damage associated with myocardial infarction or coronary artery disease by administering to a subject a composition including an effective amount of ApoD, or an active variant thereof, or an agent that increases the expression of ApoD, to thereby treat the subject at risk of tissue damage.

In another aspect, the invention relates to increasing the amount of circulating ApoD, or an active variant thereof, in a subject to reduce or treat tissue damage, by introducing a composition including ApoD, or active variant thereof into the subject, to thereby reduce tissue damage in the subject.

In another aspect, the invention relates to a method of reducing cell death associated with hypoxia in cardiomyocytes comprising contacting cardiomyocytes with a composition including an effective amount of ApoD, or an active variant thereof, to thereby reduce cell death or damage.

In some embodiments, the tissue susceptible to ischemic damage or having ischemic damage includes, for example, the heart, brain, kidney, bowel, skeletal muscle, liver, and skin. In some embodiments, the tissue damage is associated with a disease or disorder, for example, coronary artery disease, myocardial infarction, stroke, peripheral arterial disease, peripheral vascular disease, and surgery involving temporary disruption of blood flow. In some embodiments, the subject has one or more clinical indicators of coronary artery disease, such as frequency and intensity of anginal symptoms, myocardial perfusion, electrocardiogram tracings, scores on quantitative angina scales, and angiography.

In some embodiments, the methods of the invention reduce the area of tissue damage relative to the area at risk of damage by up to about 90%, up to about 80%, up to about 70%, up to about 60%, up to about 50%, up to about 40%, up to about 30%, up to about 20%, up to about 10%, or up to about 5%.

In some embodiments, ApoD, or an active variant thereof, is administered directly to damaged tissue, or tissue at risk of damage by ischemia. In some embodiments, ApoD, or an active variant thereof, is administered to a tissue other than damaged tissue or tissue at risk of damage by ischemia. In some embodiments, ApoD, or an active variant thereof, is delivered to tissue using a replication deficient viral vector, such as an adenovirus, adeno-associated virus, or lentivirus. In some embodiments, ApoD is recombinant human ApoD protein. In some embodiments, ApoD is delivered in the form of cDNA which encodes ApoD. In some embodiments, ApoD, or an active variant thereof, is directly administered to the damaged tissue, or tissue at risk of damage by ischemia.

In some embodiments, the agent that increases ApoD expression increases ApoD expression in a tissue-specific manner. Such embodiments include, but are not limited to, virus-mediated delivery of ApoD, the expression of which is controlled by a tissue-specific promoter. In some embodiments, the agent that increases ApoD expression is administered directly to the damaged tissue, or tissue at risk of damage by ischemia. In some embodiments, the agent that increases ApoD expression indirectly increases ApoD expression in a tissue-specific manner.

In some embodiments, the methods of the invention involve combination therapy with one or more therapeutic agents or treatments. Exemplary therapeutic agents or treatments include angiotensin-converting enzyme (ACE) inhibitors (e.g., enalapril, lisinopril, and captopril), angiotensin II (A-II) receptor blockers (e.g., losartan and valsartan), diuretics (e.g., bumetanide, furosemide, and spironolactone), digoxin, beta blockers, nesiritide, cholestyramine, colestipol, nicotinic acid, gemfibrozil, probucol, atorvastatin, lovastatin, aspirin, ticlopidine, clopidogrel, anti-coagulants, inhibitors of smooth muscle proliferation, inhibitors of DP1 and/or DP2 receptor, inhibitors of MAP kinase, fibroblast growth factors (e.g., FGF1, FGF2, and FGF5), vascular endothelial growth factors (VEGF) and active fragments thereof (e.g., $VEGF_{165}$), hypoxia inducible factor (HIF-1), platelet-derived growth factors (PDGF1, PDGF2), developmental embryonic locus (DEL) 1, angiopoietins, hepatocyte growth factor (HGF), monocyte chemoattractant protein (MCP-1), endothelial nitric oxide synthase (eNOS), inducible nitric oxide synthase (iNOS). Exemplary treatments include angioplasty, single coronary artery bypass grafting (CABG), or multiple CABG.

In some embodiments, ApoD, or an active variant thereof, is administered by a route selected from the group consisting of oral, intravenous injection, subcutaneous injection, intramuscular injection, myocardial injection, intrapericardial injection, endomyocardial injection, or intracoronary infusion.

In one aspect, the invention relates to the provision of an active variant of ApoD, which has an amino acid sequence at least about 70%, at least about 75%, at least about 80%, at least about 85%, at least about 90%, at least about 95%, or at least about 99% identical to wild-type mature human ApoD (SEQ ID NO: 1). In some embodiments, the active variant of ApoD is a fragment of ApoD which reduces tissue damage associated with ischemia. In some embodiments, the fragment includes at least 50, at least 100, at least 150, or at least 160 amino acids of human ApoD. In some embodiments, the active variant of ApoD has an extended serum half-life compared to wild-type ApoD. In other embodiments, ApoD is wild-type ApoD with the sequence set forth in SEQ ID NO: 1.

In another aspect, the invention relates to the use of ApoD, or an active variant thereof, or an agent that increases ApoD expression, in treating ischemic injury or ischemia/reperfusion injury in a tissue. In another aspect, the invention relates to the use of ApoD, or an active variant thereof, or an agent that increases ApoD expression, in inhibiting tissue damage associated with ischemia or ischemia/reperfusion in a subject at risk of developing tissue damage associated with ischemia or ischemia/reperfusion. In another aspect, the invention relates to the use of ApoD, or an active variant thereof, or an agent that increases ApoD expression, to increase the amount of circulating ApoD, or an active variant thereof, in a subject to inhibit, reduce, or treat tissue damage. In another aspect, the invention relates to the use of ApoD, or an active variant thereof, or an agent that increases ApoD expression, in treating tissue damage associated with myocardial infarction or coronary artery disease. In another aspect, the invention relates to the use of ApoD, or an active variant thereof, or an agent that increases ApoD expression, in inhibiting tissue damage associated with myocardial infarction or coronary artery disease in a subject at risk of developing myocardial infarction or coronary artery disease. In another aspect, the invention relates to the use of ApoD, or an active variant thereof, in reducing cell death associated with hypoxia in cardiomyocytes.

In another aspect, the invention relates to the use of ApoD, or an active variant thereof, or an agent that increases ApoD expression, for manufacturing a medicament for treating ischemic injury or ischemia/reperfusion injury in a tissue. In another aspect, the invention relates to the use of ApoD, or an active variant thereof, or an agent that increases ApoD expression, for manufacturing a medicament for inhibiting tissue damage associated with ischemia or ischemia/reperfusion in a subject at risk of developing tissue damage associated with ischemia or ischemia/reperfusion. In another aspect, the invention relates to the use of ApoD, or an active variant thereof, or an agent that increases ApoD expression, for manufacturing a medicament for increasing the amount of circulating ApoD, or an active variant thereof, in a subject to inhibit, reduce, or treat tissue damage. In another aspect, the invention relates to the use of ApoD, or an active variant thereof, or an agent that increases ApoD expression, for manufacturing a medicament for treating tissue damage associated with myocardial infarction or coronary artery disease. In another aspect, the invention relates to the use of ApoD, or an active variant thereof, or an agent that increases ApoD expression, for manufacturing a medicament for inhibiting tissue damage associated with myocardial infarction or coronary artery disease in a subject at risk of developing myocardial infarction or coronary artery disease. In another aspect, the invention relates to the use of ApoD, or an active variant thereof, for manufacturing a medicament for reducing cell death associated with hypoxia in cardiomyocytes.

BRIEF DESCRIPTION OF THE DRAWINGS

FIG. 1A is a survival curve (data from age 20 days). Arrows indicate the ages hearts were harvested. FIG. 1B is a bar graph showing heart (mg)/body weight (g) ratio at 21, 31 and 43 days (n=10, 10, and 12, respectively). FIGS. 1C-H are low (FIGS. 1C, E, and G, bar=1 mm) and high (FIGS. 1D, F, and H, bar=100 μm) magnification images of Movat pentachrome stained transverse sections of ventricles from hearts harvested at the indicated ages. Boxes in the low magnification images indicate the locations of the high magnification images. The black and white stars indicate the left and right ventricles, respectively. The arrows and arrowheads indicate microscopic scarring.

FIG. 2A is a graph showing temporal mRNA expression of ApoD in hearts of dKO and Het mice (dKO, black diamonds; Het, gray circles) (mean values from microarray analysis). FIGS. 2B-D show data of temporal mRNA expression of ApoD, Mpeg1, and Alas2, respectively, in wild type mice subjected to coronary artery ligation from microarray data in the Cardiogenomics study (26, 27) (black circles, infracted tissue; gray triangles, non-infarcted tissue; black squares, control sham operation). Error bars represent SEM.

FIGS. 5A and 5B are bar graphs showing total cell number and viability (trypan blue exclusion) at the end of the reoxygenation period. Error bars represent SEM. (*, P<0.0005; **, P<0.0001.)

DETAILED DESCRIPTION OF THE INVENTION

Figure 1:
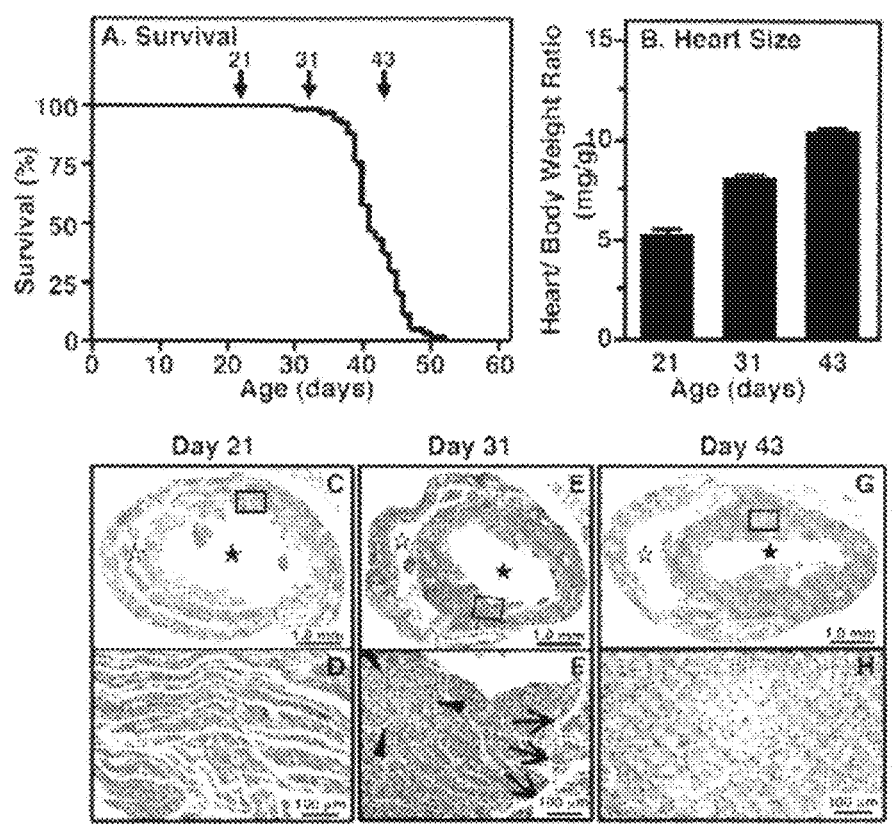
FIG. 1 presents analyses of hearts of $SR-BI^{-/-}/apoE^{-/-}$ ('dKO') mice harvested at 21, 31 and 43 days of age. dKO mice were maintained on a standard chow diet.

Terms used in the claims and specification are defined as set forth below unless otherwise specified.

I. Definitions

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "Apolipoprotein D" or "ApoD" refers both to the naturally-occurring amino sequence of the protein, and to variants (i.e., active variants) in which there are one or more mutations which do not substantially alter the conformation or biological activity of the molecule. Human ApoD exists as a precursor of 189 amino acids (SEQ ID NO: 3), and a mature form of 169 amino acids (SEQ ID NO: 1). Unless otherwise specified, "ApoD" will refer to the naturally occurring amino acid sequence of mature human ApoD is set forth in SEQ ID NO: 1. The nucleic acid sequences of the mature form of human ApoD and the human ApoD precursor are set forth in SEQ ID NOs: 2 and 4, respectively.

As used herein, the term "active variant" refers to a polypeptide that is a variant of a selected protein (e.g., a native or wildtype protein) that retains a relevant biological activity, e.g., reduction of ischemic damage to tissue. For the purposes of this invention, an active variant also encompasses an "active fragment" or "mimetic" of a protein (e.g., ApoD) that retains a relevant biological activity, e.g., reduction of ischemic damage to tissue. An active variant can differ from the selected protein at one or more residues, e.g., can have one or more conservative amino acid substitutions. An active variant can be a naturally occurring polypeptide, e.g., a polypeptide that occurs in nature (e.g., a natural protein), or a genetically modified variant that exhibits cardioprotective activity. As one example, an active variant of ApoD can be at least 70%, 75%, 80%, 85%, 90%, 95%, or 99% identical to the sequence of wild-type ApoD, e.g., SEQ ID NO: 1, and retains the ability to reduce ischemic tissue damage in the heart in response to ischemia/reperfusion stress, or protect cardiomyocytes from, e.g., hypoxia-induced apoptosis. Active variants include homologs of ApoD that retain cardioprotective activity.

As used herein, the term "active fragment" refers to a polypeptide that is a portion of a larger protein (e.g., full length wild-type ApoD) that retains some or all of a relevant biological activity, e.g., cardioprotective ability. The active fragment can also be a variant, e.g., can differ from the selected protein at one or more residues, e.g., can have one or more conservative amino acid substitutions. As an example, the active fragment can have at least 50, at least 100, at least 150, or at least 160 amino acids of human ApoD. Routine methods in the art and those described infra can be used to determine whether a fragment of, e.g., ApoD, has cardioprotective effects.

As used herein, the terms "mimetic," "peptide mimetic," "peptidomimetic," "organomimetic," and "chemical mimetic" are intended to encompass peptide derivatives, peptide analogs, and chemical compounds having an arrangement of atoms in a three-dimensional orientation that is equivalent to that of a peptide of the present invention or has a biological activity having similarity to that of ApoD or an ApoD variant. A mimetic is also intended to encompass molecules (e.g., small molecules) that do not have an equivalent structure as ApoD or an active ApoD variant, but increase the expression of ApoD in a subject to result in a similar biological activity as ApoD or an active ApoD variant. It will be understood that the phrase "equivalent to" as used herein is intended to encompass peptides having substitution(s) of certain atoms, or chemical moieties in said peptide, having bond lengths, bond angles, and arrangements in the mimetic peptide that produce the same or sufficiently similar arrangement or orientation of said atoms and moieties to have the biological function of the peptides of the invention. In peptide mimetics, the three-dimensional arrangement of the chemical constituents may be structurally and/or functionally equivalent to the three-dimensional arrangement of the peptide backbone and component amino acid sidechains in the peptide, resulting in such peptido-, organo-, and chemical mimetics of the peptides of the invention having substantial biological activity. These terms are used according to the understanding in the art, as illustrated, for example, by Fauchere, (Adv. Drug Res. 15:29, 1986); Veber & Freidinger, (TINS p. 392, 1985); and Evans et al., (J. Med. Chem. 30:1229, 1987), incorporated herein by reference. U.S. Pat. No. 5,637,677, for example, describes methods for producing mimetics.

As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 1981; 2:482, by the homology alignment algorithm of Needleman & Wunsch, *J Mol Biol* 1970; 48:443, by the search for similarity method of Pearson & Lipman, *PNAS* 1988; 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al. *J Mol Biol* 1990; 215:403-10. Software for performing BLAST analyses is publicly available through the National Center for Biotechnology Information website.

As used herein, the term "ischemia" generally relates to physiological damage resulting from a lack of blood and oxygen flow.

As used herein, "myocardial ischemia" refers to a condition within the heart that results from a deficient supply of blood to the myocardium. Ischemia can involve, for example, restricted blow flow to the heart tissue as a result of blockage or reduced flow through one or more coronary arteries that normally supplies the heart tissue. An infarction results when the blood supply to a localized area is deprived for a prolonged period of time so that heart cells die.

As used herein, "reperfusion injury" refers to the cellular changes and tissue damage seen after a period of total ischemia followed by reperfusion. Extremity replantation, organ transplantation, free flap tissue reconstruction, myocardial infarction and stroke are all clinical examples of tissue ischemia which can lead to tissue loss due to reperfusion injury after blood flow is reestablished. Tissue reperfusion injury, seen in its full clinical extent as the no-reflow phenomenon, appears as an inflammatory response to reperfusion resulting in the ultimate death of the tissue.

As used herein, "hypoxia" relates to a deficiency of oxygen reaching the tissues of the body.

As used herein, "coronary artery disease" or "coronary heart disease" refers to disorders and conditions generally recognized by those skilled in the art as related to the deposition of atheroma in the large- and medium-sized arteries serving the heart. Thus, coronary artery disease means clinical syndromes (including, but not limited to, angina, myocardial infarction, unstable angina, and sudden ischemic death) which are based on the pathology of coronary artery atheroma.

As used herein, "occlusive peripheral vascular disease" (also known as peripheral arterial occlusive disorder) is a vascular disorder involving blockage in the carotid or femoral arteries, including the iliac artery. Blockage in the femoral arteries causes pain and restricted movement. A specific disorder associated with occlusive peripheral vascular disease is diabetic foot, which affects diabetic patients, often resulting in amputation of the foot.

As used herein, the term "stroke" relates to physiological damage resulting from a lack of blood and oxygen flow to the brain.

"Carriers" or "pharmaceutically acceptable carriers" used in the methods of the invention are conventional. Remington's Pharmaceutical Sciences, by E. W. Martin, Mack Publishing Co., Easton, Pa., 15th Edition (1975), describes compositions and formulations suitable for pharmaceutical delivery of the proteins and other compositions herein disclosed. In general, the nature of the carrier will depend on the particular mode of administration being employed.

"Purified," as used herein, does not require absolute purity. Rather, it is intended as a relative term. Thus, for example, a purified protein is one in which the protein is more enriched than the protein is in its natural environment within a cell. Preferably, a preparation is purified such that the protein represents at least 50% of the protein content of the preparation. The immunogenic polypeptides disclosed herein, or antibodies that specifically bind the disclosed immunogenic polypeptides, can be purified by any of the means known in the art. See, e.g., Guide to Protein Purification, ed. Deutscher, Meth. Enzymol. 185, Academic Press, San Diego, 1990; and Scopes, Protein Purification: Principles and Practice, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

A "virus" consists essentially of a core of nucleic acid surrounded by a protein coat, and has the ability to replicate only inside a living cell.

"Administration" refers to the introduction of a composition into a subject by a chosen route. For example, if the chosen route is intravenous, the composition is administered by introducing the composition into a vein of the subject. Other exemplary routes of administration include intranasal, intramuscular, and subcutaneous administration.

As used herein, "pharmacokinetic group" refers to a protein, peptide, or moiety that increases the circulation half-life of a biologically active molecule when fused to or administered together with the biologically active molecule. Examples of pharmacokinetic groups include, but are not limited to, polyethylene glycol (PEG), human serum albumin (HSA) binders (see, e.g., US2005/0287153, US2007/0003549, WO2009/083804, WO2009/133208, and SABA molecules in US2012/094909), HSA, Fc or Fc fragments and variants thereof, transferrin and variants thereof, and sugars (e.g., sialic acid). Other exemplary extended-PK groups are disclosed in Kontermann et al., *Current Opinion in Biotechnology* 2011; 22:868-876.

As used herein, "half-life" refers to the time taken for the serum or plasma concentration of a polypeptide to reduce by 50%, in vivo, for example due to degradation and/or clearance or sequestration by natural mechanisms.

As used herein, "therapeutic protein" refers to any polypeptide, protein, protein variant, fusion protein and/or fragment thereof which may be administered to a subject as a medicament. Exemplary therapeutic proteins with cardioprotective properties are VEGF and FGF.

A "therapeutic agent," when used in a generic sense, includes treating agents and prophylactic agents.

An "effective amount" or "therapeutically effective amount" refers to an amount that is effective to achieve a desired result, e.g., reduce tissue damage to the heart associated with myocardial ischemia. When administered to a subject, a dosage will generally be used that will achieve target tissue concentrations shown to achieve a desired in vitro effect. A therapeutically effective amount of a substance, such as ApoD, or an active variant thereof, can be administered in a single dose, or in several doses, e.g., daily, during a course of treatment. However, the effective amount of a composition will be dependent on the compound applied, the subject being treated, the severity and type of the affliction, and the manner of administration of the composition.

The term "sufficient amount" means an amount sufficient to produce a desired effect, e.g., an amount sufficient to reduce tissue damage to the heart associated with myocardial ischemia.

The term "prophylactic" or "preventive" refers to the decrease in risk of onset of a phenomenon, for example a pathology.

The term "treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, e.g., by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment, or "prophylaxis" is a treatment administered to an at risk subject, i.e., a subject who may not exhibit signs of disease or exhibits early signs of disease and treatment is for the purpose of decreasing the risk of developing pathology.

As used herein, "combination therapy" embraces administration of each agent or therapy in a sequential or simultaneous manner in a regiment that will provide beneficial effects of the combination, and co-administration of these agents or therapies in a substantially simultaneous. Combination therapy also includes combinations where individual elements may be administered at the same or different times and/or by the same or different routes but which act in combination to provide a beneficial effect by co-action or pharmacokinetic and pharmacodynamics effect of each agent or tumor treatment approaches of the combination therapy.

The term "mammal" or "subject" or "patient" as used herein includes both humans and non-humans and include, but is not limited to, humans, non-human primates, canines, felines, murines, bovines, equines, and porcines.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

II. Overview

Ischemia results from a decrease or lack of blood flow and oxygen to parts of the body, such as the heart or brain, resulting in damage to tissue distal to a blockage. In the context of surgery, certain procedures such as cardiac surgery and organ transplantation involve halting the flow of blood temporarily and subsequent resumption (reperfusion), resulting in ischemia-reperfusion injury. During a heart attack, the flow of blood supplying the heart stops, resulting in ischemia that can lead to infarction (myocardial infarction).

To date, many studies have treated serum levels of ApoD as a marker for disease states including, e.g., Alzheimer's Disease and Parkinson's Disease. The present invention is based, in part, on the unexpected discovery that ApoD is effective in treating and reducing tissue damage associated with ischemia/reperfusion injury, such as that associated with myocardial infarction. Treatment occurs even when the source of ApoD is generalized, such as, for example by production in the liver following injection of ApoD expressing virus, indicating that circulating ApoD results in a tissue- or cardioprotective effect. The protective role of ApoD is further indicated by the exacerbation of cardiac tissue damage resulting from ischemia/reperfusion injury in ApoD knockout mice. A protective effect on cardiomyocytes from hypoxia/reoxygenation injury in culture was also demonstrated by exogenous ApoD. The protective effect was dependent on ApoD conformation, which correlated with its antioxidation activity. Without being bound by theory, the tissue protective properties of ApoD may involve the antioxidant potential of ApoD and/or the ability of ApoD to scavenge toxic small molecules released from stressed cells, or other mechanisms.

Accordingly, the present invention, in general, relates to methods of reducing or treating tissue damage resulting from impaired blood flow by administering an effective amount of ApoD, or an active variant thereof, or an agent that increases the expression of ApoD, to reduce the tissue damage.

In one aspect, the invention relates to the treatment of ischemic injury in a tissue by administering to a subject a composition including an effective amount of ApoD, or an active variant thereof, or an agent that increases the expression of ApoD, to thereby treat ischemic injury in the tissue or to protect uninjured tissue from ischemic injury.

In another aspect, the invention relates to the treatment of ischemia/reperfusion injury in a tissue by administering to a subject a composition including an effective amount of ApoD, or an active variant thereof, or an agent that increases the expression of ApoD, to thereby treat ischemia/reperfusion injury in the tissue.

In another aspect, the invention relates to prophylactic methods, i.e., methods of treating a subject at risk of tissue damage associated with ischemia or ischemia/reperfusion, by administering to a subject a composition including an effective amount of ApoD, or an active variant thereof, or an agent that increases the expression of ApoD, to thereby treat the subject at risk of tissue damage. Such subjects can be readily identified in the clinical context as being scheduled to undergo or are undergoing surgery that involves halting blood flow, or as having risk factors (e.g., genetic predisposition) associated with a particular disease state (e.g., coronary artery disease).

In another aspect, the invention relates to treating tissue damage associated with coronary artery disease, by administering to a subject a composition including an effective amount of ApoD, or an active variant thereof, or an agent that increases the expression of ApoD, to thereby treat tissue damage in the subject. In another aspect, the invention relates to treating tissue damage associated with myocardial infarction, by administering to a subject a composition including an effective amount of ApoD, or an active variant thereof, or an agent that increases the expression of ApoD, to thereby treat tissue damage in the subject. Such subjects can be readily identified in the clinical context with risk factors associated with coronary heart disease or myocardial infarction, as described infra.

In another aspect, the invention relates to treating a subject at risk of tissue damage associated with coronary artery disease by administering to a subject a composition including an effective amount of ApoD, or an active variant thereof, or an agent that increases the expression of ApoD, to thereby treat the subject at risk of tissue damage. In another aspect, the invention relates to treating a subject at risk of tissue damage associated with myocardial infarction by administering to a subject a composition including an effective amount of ApoD, or an active variant thereof, or an agent that increases the expression of ApoD, to thereby treat the subject at risk of tissue damage.

In another aspect, the invention relates to increasing the amount of circulating ApoD, or an active variant thereof, in a subject to reduce or treat tissue damage, by introducing a composition including ApoD, or active variant thereof into the subject, to thereby reduce tissue damage in the subject.

In another aspect, the invention relates to a method of reducing cell death associated with hypoxia in cardiomyocytes comprising contacting cardiomyocytes with a composition including an effective amount of ApoD, or an active variant thereof, to thereby reduce cell death or damage.

In some embodiments, the tissue susceptible to ischemic damage or having ischemic damage includes, for example, the heart, brain, kidney, bowel, skeletal muscle, liver, and skin. In some embodiments, the tissue damage is associated with a disease or disorder, for example, coronary artery disease, myocardial infarction, stroke, peripheral arterial disease, peripheral vascular disease, and surgery involving temporary disruption of blood flow. In some embodiments, the subject has one or more clinical indicators of coronary artery disease, such as frequency and intensity of anginal symptoms, myocardial perfusion, electrocardiogram tracings, scores on quantitative angina scales, and angiography.

In some embodiments, the methods of the invention reduce the area of tissue damage relative to the area at risk of damage by up to about 90%, up to about 80%, up to about 70%, up to about 60%, up to about 50%, up to about 40%, up to about 30%, up to about 20%, up to about 10%, or up to about 5%.

In some embodiments, ApoD, or an active variant thereof, is administered directly to damaged tissue, or tissue at risk of damage by ischemia. In some embodiments, ApoD, or an active variant thereof, is administered to a tissue other than damaged tissue or tissue at risk of damage by ischemia, e.g., the liver or blood. In some embodiments, ApoD, or an active variant thereof, is delivered to tissue using a replication deficient viral vector, such as an adenovirus, adeno-associated virus, or lentivirus. In some embodiments, ApoD is recombinant human ApoD protein. In some embodiments, ApoD is delivered in the form of cDNA which encodes ApoD. In some embodiments, ApoD, or an active variant thereof, is directly administered to the damaged tissue, or tissue at risk of damage by ischemia.

In some embodiments, the agent that increases ApoD expression increases ApoD expression in a tissue-specific manner. Such embodiments include, but are not limited to, virus-meditated delivery of ApoD, the expression of which is controlled by a tissue-specific promoter. In some embodiments, the agent that increases ApoD expression is administered directly to the damaged tissue, or tissue at risk of damage by ischemia. In some embodiments, the agent that increases ApoD expression indirectly increase ApoD expression in a tissue-specific manner.

In some embodiments, the methods of the invention involve combination therapy with one or more therapeutic agents or treatments. Exemplary therapeutic agents or treatments include angiotensin-converting enzyme (ACE) inhibitors (e.g., enalapril, lisinopril, and captopril), angiotensin II (A-11) receptor blockers (e.g., losartan and valsartan), diuretics (e.g., bumetanide, furosemide, and spironolactone), digoxin, beta blockers, nesiritide, cholestyramine, colestipol, nicotinic acid, gemfibrozil, probucol, atorvastatin, lovastatin, aspirin, ticlopidine, clopidogrel, anti-coagulants, inhibitors of smooth muscle proliferation, inhibitors of DP1 and/or DP2 receptor, inhibitors of MAP kinase, fibroblast growth factors (e.g., FGF1, FGF2, and FGF5), vascular endothelial growth factors (VEGF) and active fragments thereof (e.g., $VEGF_{165}$), hypoxia inducible factor (HIF-1), platelet-derived growth factors (PDGF1, PDGF2), developmental embryonic locus (DEL) 1, angiopoietins, hepatocyte growth factor (HGF), monocyte chemoattractant protein (MCP-1), endothelial nitric oxide synthase (eNOS), inducible nitric oxide synthase (iNOS). Exemplary treatments include angioplasty, single coronary artery bypass grafting (CABG), or multiple CABG.

In some embodiments, ApoD, or an active variant thereof, is administered by a route selected from the group consisting of oral, intravenous injection, subcutaneous injection, intramuscular injection, myocardial injection, intrapericardial injection, endomyocardial injection, or intracoronary infusion.

In one aspect, the invention relates to the provision of an active variant of ApoD, which has an amino acid sequence at least about 70%, at least about 75%, at least about 80%, at least about 85%, at least about 90%, at least about 95%, or at least about 99% identical to wild-type mature human ApoD (SEQ ID NO: 1). In some embodiments, the active variant of ApoD is a fragment of ApoD which reduces tissue damage associated with ischemia. In some embodiments, the fragment includes at least 50, at least 100, at least 150, or at least 160 amino acids of human ApoD. In some embodiments, the active variant of ApoD has an extended serum half-life compared to wild-type ApoD. In other embodiments, ApoD is wild-type ApoD with the sequence set forth in SEQ ID NO: 1.

In another aspect, the invention relates to the use of ApoD, or an active variant thereof, or an agent that increases ApoD expression, in treating ischemic injury in a tissue. In another aspect, the invention relates to the use of ApoD, or an active variant thereof, or an agent that increases ApoD expression, in treating ischemia/reperfusion injury in a tissue. In another aspect, the invention relates to the use of ApoD, or an active variant thereof, or an agent that increases ApoD expression, in inhibiting tissue damage associated with ischemia or ischemia/reperfusion in a subject at risk of developing tissue damage associated with ischemia or ischemia/reperfusion. In another aspect, the invention relates to the use of ApoD, or an active variant thereof, or an agent that increases ApoD expression, to increase the amount of circulating ApoD, or an active variant thereof, in a subject to inhibit, reduce, or treat tissue damage. In another aspect, the invention relates to the use of ApoD, or an active variant thereof, or an agent that increases ApoD expression, in treating tissue damage associated with coronary artery disease. In another aspect, the invention relates to the use of ApoD, or an active variant thereof, or an agent that increases ApoD expression, in treating tissue damage associated with myocardial infarction. In another aspect, the invention relates to the use of ApoD, or an active variant thereof, or an agent that increases ApoD expression, in inhibiting tissue damage associated with coronary artery disease in a subject at risk of developing coronary artery disease. In another aspect, the invention relates to the use of ApoD, or an active variant thereof, or an agent that increases ApoD expression, in inhibiting tissue damage associated with myocardial infarction in a subject at risk of developing myocardial infarction. In another aspect, the invention relates to the use of ApoD, or an active variant thereof, in reducing cell death associated with hypoxia in cardiomyocytes.

In another aspect, the invention relates to the use of ApoD, or an active variant thereof, or an agent that increases ApoD expression, for manufacturing a medicament for treating ischemic injury in a tissue. In another aspect, the invention relates to the use of ApoD, or an active variant thereof, or an agent that increases ApoD expression, for manufacturing a medicament for treating ischemia/reperfusion injury in a tissue. In another aspect, the invention relates to the use of ApoD, or an active variant thereof, or an agent that increases ApoD expression, for manufacturing a medicament for inhibiting tissue damage associated with ischemia or ischemia/reperfusion in a subject at risk of developing tissue damage associated with ischemia or ischemia/reperfusion. In another aspect, the invention relates to the use of ApoD, or an active variant thereof, or an agent that increases ApoD expression, for manufacturing a medicament for increasing the amount of circulating ApoD, or an active variant thereof, in a subject to inhibit, reduce, or treat tissue damage. In another aspect, the invention relates to the use of ApoD, or an active variant thereof, or an agent that increases ApoD expression, for manufacturing a medicament for treating tissue damage associated with coronary artery disease. In another aspect, the invention relates to the use of ApoD, or an active variant thereof, or an agent that increases ApoD expression, for manufacturing a medicament for treating tissue damage associated with myocardial infarction. In another aspect, the invention relates to the use of ApoD, or an active variant thereof, or an agent that increases ApoD expression, for manufacturing a medicament for inhibiting tissue damage associated with coronary artery disease in a subject at risk of developing coronary artery disease. In another aspect, the invention relates to the use of ApoD, or an active variant thereof, or an agent that increases ApoD expression, for manufacturing a medicament for inhibiting tissue damage associated with myocardial infarction in a subject at risk of developing myocardial infarction. In another aspect, the invention relates to the use of ApoD, or an active variant thereof, for manufacturing a medicament for reducing cell death associated with hypoxia in cardiomyocytes.

III. ApoD, Active Variants, Fusions, and Activators

The methods of the invention involve the use of ApoD, or an active variant thereof, to treat or prevent tissue damage associated with ischemia (e.g., myocardial infarction or coronary arterial disease).

In some embodiments, the methods of the invention involve the use of wild-type mature human ApoD which has the sequence set forth in SEQ ID NO: 1. Recombinant human ApoD is available from multiple commercial sources (e.g., Origene, Fitzgerald Industries, Capital Biosciences).

In some embodiments, the methods of the invention use wild-type human ApoD fused to a pharmacokinetic moiety, as discussed infra. In some embodiments, wild-type human ApoD includes an epitope tag.

Active ApoD variants are contemplated for use in the methods of the invention. Preferably, such active variants retain the cardioprotective properties of wild-type ApoD, and can be ApoD mutant polypeptides, e.g., a wild-type ApoD sequence with one or more mutations, ApoD polypeptide fragments, e.g., a portion of the ApoD polypeptide that retains cardioprotective activity, or an ApoD mimetic.

An active ApoD variant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to wild-type ApoD, and preferably retains or increases the cardioprotective activity of wild-type ApoD, as assessed by one or more assays described infra.

Active ApoD variants can be at least about 70%, at least about 75%, at least about 80%, at least about 85%, at least about 90%, at least about 95%, or at least about 99% identical to wild-type human ApoD (SEQ ID NO: 1). The mutation can consist of a change in the number or content of amino acid residues. For example, the active ApoD variants can have a greater or a lesser number of amino acid residues than wild-type ApoD. Alternatively, or in addition, active ApoD variants can contain a substitution of one or more amino acid residues that are present in the wild-type ApoD.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine.

Exemplary ApoD variants include those disclosed in, e.g., Bhatia et al., Biochem J 2012; 442:713-21, which retain antioxidant activity (e.g., substitution of methionine residues at amino acid 49 and/or 157 of SEQ ID NO: 1 with alanine).

Aglycosylated ApoD variants are also contemplated for use in the methods of the invention. ApoD has two evolutionarily conserved N-glycosylation sites (Asn 45 and Asn 78 in humans), which can be substituted individually or in combination with an amino acid that cannot be glycosylated. Alternatively, ApoD, or an active variant thereof, can be obtained in aglycosylated form by producing the ApoD, or active variant thereof, in, e.g., prokaryotic cells (e.g., E. coli). It has been hypothesized that N-glycosylation modulates ApoD protein folding, resulting in conformational changes favorable for binding to its physiological ligands or association with HDL. The protective effects of such variants against ischemic and hypoxic stress can be assessed using the methods described infra.

In general, ApoD, or an active variant thereof, for use in the methods of the invention will be synthetic, or produced by expression of a recombinant nucleic acid molecule. Techniques for making ApoD, or an active variant thereof, are routine in the art. For example, a mutation that consists of a substitution of one or more of the amino acid residues in ApoD can be created using art-recognized PCR-based mutagenesis. Kits are commercially available for such purposes (e.g., QuickChange II Site-Directed Mutagenesis Kit™ from Strategene). Mutations that consist of deletions or additions of amino acid residues to ApoD, or an active variant thereof, can also be made with standard recombinant techniques. When introducing deletions or additions, the nucleic acid molecule encoding ApoD is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

ApoD, or an active variant thereof, can also be chemically synthesized using art-recognized methods.

In some embodiments, ApoD, or an active variant thereof, can also include a heterologous polypeptide (i.e., a polypeptide that is not ApoD). Such heterologous polypeptides can increase the circulating half-life of the chimeric polypeptide in vivo, and may, therefore, further enhance the properties of ApoD, as discussed infra. Such heterologous polypeptides can be fused to ApoD, or an active variant thereof, using standard art-recognized methods.

In other embodiments, ApoD, or an active variant thereof, can include a polypeptide that functions as an antigenic tag, such as a FLAG™ sequence. Other antigenic tags well known in the art include, e.g., hemagglutinin (HA), myc, glutathione S transferase (GST), hexahistidine, and OLLAS.

Chimeric polypeptides can be constructed using no more than conventional molecular biological techniques, which are well within the ability of those of ordinary skill in the art to perform.

In some embodiments, the active ApoD variants are active fragments of ApoD, i.e., polypeptide fragments of ApoD that retain cardioprotective properties. Whether a particular ApoD fragment retains or has increased activity relative to wild-type ApoD can be tested using assays discussed infra. Accordingly, in some embodiments, the active ApoD variant will be at least 10, at least 20, at least 30, at least 40, at least 50, at least 60, at least 70, at least 80, at least 90, at least 100, at least 110, at least 120, at least 130, at least 140, at least 150, at least 160, 161, 162, 163, 164, 165, 166, 167, or at least 168 amino acids in length. The generation of active fragments of ApoD is routine in the art. An exemplary active fragment of ApoD, in which the first two residues of the mature ApoD sequence, Glu-Ala, are deleted (i.e., resulting in a 167 amino acid protein), is disclosed in Eichinger et al., JBC 2007; 282:31068-75.

ApoD mimetics (e.g., peptide mimetics, chemical mimetics, and organomimetics) are also contemplated for use in the methods of the invention. In some embodiments, the mimetics are peptide mimetics that mimic the three-dimensional structure of ApoD. Such peptide mimetics may have significant advantages over naturally occurring ApoD including, for example, more economical production, greater chemical stability, enhanced pharmacological properties (half-life, absorption, potency, efficacy, etc.), altered specificity, reduced antigenicity and others. In some embodiments, the mimetics are peptide-containing molecules that mimic elements of the secondary structure of ApoD. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. In other embodiments, peptide analogs are commonly produced in the pharmaceutical industry as non-peptide drugs with properties analogous to those of the template peptide. These types of non-peptide compounds are also referred to as peptide mimetics or peptidomimetics (Fauchere, Adv Drug Res 1986; 15:29-69; Veber & Freidinger, Trends Neurosci 1985: 8; 392-6; Evans et al., J Med Chem 1987:30; 1229-39 which are incorporated herein by reference).

Peptide mimetics structurally similar to ApoD may be used to produce an equivalent therapeutic or prophylactic effect. Generally, peptide mimetics are structurally similar to a paradigm polypeptide (i.e., a polypeptide that has a biochemical property or pharmacological activity), but have one or more peptide linkages optionally replaced by a linkage by methods known in the art. Labeling of peptide mimetics usually involves covalent attachment of one or more labels, directly or through a spacer (e.g., an amide group), to non-interfering positions on the peptide mimetic that are predicted by quantitative structure-activity data and molecular modeling. Such non-interfering positions generally are positions that do not form direct contacts with the macromolecules to which the peptide mimetic binds to produce the therapeutic effect. Derivitization (e.g., labeling) of peptide mimetics should not substantially interfere with the desired biological or pharmacological activity of the peptide mimetic.

The use of peptide mimetics can be enhanced through the use of combinatorial chemistry to create drug libraries. The design of peptide mimetics can be aided by identifying amino acid mutations that increase or decrease binding of a peptide to, for instance, an ApoD ligand. Such interactions can be determined using, e.g., yeast two hybrid assays, phage display, or standard co-immunoprecipitation techniques. These methods allow positive and negative selection for peptide-protein interactions and the identification of the sequences that determine these interactions.

In some embodiments, the mimetics are organomimetics or chemical mimetics. Such mimetics can be obtained, e.g., by using the principles of conventional or rational drug design (see, e.g., Andrews, et al., Proc. Alfred Benzon Symp. 28:145-165, 1990; McPherson, Eur. J. Biochem. 189:1-24, 1990; HoI, et al., in Molecular Recognition: Chemical and Biochemical Problems, (Roberts, ed.); Royal Society of Chemistry; pp. 84-93, 1989a; HoI, Arzneim-Forsch. 39:1016-1018, 1989b; HoI, Agnew Chem. Int. Ed. Engl. 25:767-778, 1986). In accordance with the methods of conventional drug design, the desired mimetic molecules may be obtained by randomly testing molecules whose structures have an attribute in common with the structure of a "native" peptide. The quantitative contribution that results from a change in a particular group of a binding molecule may be determined by measuring the biological activity of the putative mimetic in comparison with the activity of the peptide using the methods described infra. In one embodiment of rational drug design, the mimetic is designed to share an attribute of the most stable three-dimensional conformation of the peptide. Thus, for example, the mimetic may be designed to possess chemical groups that are oriented in a way sufficient to cause ionic, hydrophobic, or van der Waals interactions that are similar to those exhibited by the peptides of the invention, as disclosed herein.

One method for performing rational mimetic design employs a computer system capable of forming a representation of the three-dimensional structure of the peptide. Molecular structures of the peptide mimetics, organomimetics, and chemical mimetics of ApoD may be produced using computer-assisted design programs commercially available in the art. Examples of such programs include SYBYL 6.5®, HQSAR™, and ALCHEMY 2000™ (Tripos); GALAXY™ and AM2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.); and CHEMBUILDER3D™ (Interactive Simulations, Inc., San Diego, Calif.).

As described above, the peptide mimetics, organomimetics, and chemical mimetics may be produced using conventional chemical synthetic techniques, for example, designed to accommodate high throughput screening, including combinatorial chemistry methods. Combinatorial methods useful in the production of the peptide mimetics, organomimetics, and chemical mimetics include phage display arrays, solid-phase synthesis, and combinatorial chemistry arrays, as provided, for example, by SIDDCO (Tucson, Ariz.); Tripos, Inc.; Calbiochem/Novabiochem (San Diego, Calif.); Symyx Technologies, Inc. (Santa Clara, Calif.); Medichem Research, Inc. (Lemont, Ill.); Pharm-Eco Laboratories, Inc. (Bethlehem, Pa.); or N.V. Organon (Oss, Netherlands). Combinatorial chemistry production of the peptide mimetics, organomimetics, and chemical mimetics of the invention may be produced according to methods known in the art, including, but not limited to, techniques disclosed in Terrett, (Combinatorial Chemistry, Oxford University Press, London, 1998); Gallop, et al., J. Med. Chem. 37:1233-51, 1994; Gordon, et al., J. Med. Chem. 37:1385-1401, 1994; Look, et al., Bioorg. Med. Chem. Lett. 6:707-12, 1996; Ruhland, et al., J. Amer. Chem. Soc. 118: 253-4, 1996; Gordon, et al., Ace. Chem. Res. 29:144-54, 1996; Thompson & Ellman, Chem. Rev. 96:555-600, 1996; Fruchtel & Jung, Angew. Chem. Int. Ed. Engl. 35:17-42, 1996; Pavia, "The Chemical Generation of Molecular Diversity", Network Science Center, www.netsci.org, 1995; Adnan, et al., "Solid Support Combinatorial Chemistry in Lead Discovery and SAR Optimization," Id., 1995; Davies and Briant, "Combinatorial Chemistry Library Design using Pharmacophore Diversity," Id., 1995; Pavia, "Chemically Generated Screening Libraries: Present and Future," Id., 1996; and U.S. Pat. No. 5,880,972; U.S. Pat. No. 5,463,564; U.S. Pat. No. 5,331,573; and U.S. Pat. No. 5,573,905.

Pharmacokinetic Moieties

In some embodiments, the serum half-life of ApoD, or an active variant thereof, is extended by fusion with art-recognized pharmacokinetic moieties using standard methods known in the art. Non-limiting examples of pharmacokinetic moieties include Fc domains (e.g., of human immunoglobulin) and art-recognized Fc mutants that increase the half-life of their fusion partners (see, e.g., US 2003/0108548, US2007/0111281, US2006/0235208, U.S. Pat. No. 5,624,821, WO2005037867, WO05/018572, U.S. Pat. No. 7,217,798, U.S. Pat. No. 8,318,907, US20120276097, US20120276092, US20120128663), PEGylation (see, e.g., U.S. Pat. No. 7,610,156, U.S. Pat. No. 7,847,062, EP-A 0 473 084 and U.S. Pat. No. 5,932,462,), serum albumin (see, e.g., US2010/0144599, US2007/0048282, and US2011/0020345), serum albumin binding proteins (see, e.g., US2005/0287153, US2007/0003549, US2007/0178082, US2007/0269422, US2010/0113339, WO2009/083804, and WO2009/133208), serum immunoglobulin binding proteins (see, e.g, US2007/0178082), transferrin and variants thereof (see, e.g., US20060130158), and fibronectin (Fn)-based scaffold domain proteins that bind serum albumin (see, e.g., US2012/0094909). Pharmacokinetic moieties can be fused to ApoD, or an active variant thereof, with or without a linker using standard recombinant methods.

In some embodiments, the serum half-life of ApoD, or an active variant thereof, is increased relative to ApoD alone (i.e., ApoD not fused to a pharmacokinetic moiety). In certain embodiments, the serum half-life of ApoD, or an active variant thereof, fused to or modified with a pharmacokinetic moiety is at least 20, 40, 60, 80, 100, 120, 150, 180, 200, 400, 600, 800, or 1000% longer relative to the serum half-life of ApoD alone. In other embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, or 10-fold greater than the serum half-life of ApoD alone.

In some embodiments, the protein half-life is determined in vitro, such as in a buffered saline solution or in serum. In other embodiments, the protein half-life is an in vivo circulation half-life, such as the half-life of the protein in the serum or other bodily fluid of an animal. Such methods are routine in the art.

Activators of ApoD

A number of molecules (e.g., small molecules) and proteins are known to induce ApoD expression in cultured cells and in vivo. For example, androgens (dihydrotestosterone and testosterone) increase ApoD secretion by prostate cancer cells (Simard et al., *Cancer Res* 1991; 51:4336-41), liver X receptor (LXR) agonist GW3965 increases expression of ApoD in fat and skeletal muscle (Hummasti et al., *J Lipid Res* 2004:45:616-25), and 1,25-dihydroxyvitamin D3 strongly up-regulates ApoD mRNA levels in breast cancer cells (Lopez-Boado et al., *Cancer Res* 1997; 57:4091-7).

Other exemplary molecules known to increase ApoD expression include dihydrotestosterone (DHT) (Blais et al., *Int J Cancer* 1994; 59:400-7; Blais et al., *Int J Cancer* 1995; 62:732-7; Chen et al., *Mol Cell Biochem* 2011; 354:311-6), IL-1 (Blais et al., 1994; Blais et al., 1995), dexamethasone (Blais et al., 1994; Blais et al., 1995), all-trans-retinoic acid (RA) (Lopez-Boado et al., *JBC* 1994; 269:26871-8), pituitary adenylate cyclase-activating peptide (PACAP) (Kosacka et al., *Neurosci Res* 2011; 69:8-16), and TAp73 and TAp63 (Sasaki et al., *JBC* 2009; 284:872-83). Accordingly, the use of ApoD activators capable of modulating, and in particular activating, the expression and/or the biological activity of ApoD, are also contemplated for use in the methods of the invention. Such molecules and proteins can be used to increase either systemic production or local cardiac production of ApoD at sufficient levels to confer cardioprotection.

In some embodiments, ApoD can be used as a tool for screening biological or chemical compounds in peptide or chemical libraries that are capable of modulating, and in particular of activating, the expression and/or the biological activity of ApoD. Such compounds (peptide or non-peptide) can be screened using art-recognized methods or the in vitro assays described infra. For example, a chemical or peptide library can be used to screen for compounds that increase the cardio-protective effects of ApoD in cultured cardiomyocytes subjected to hypoxia. Preferably, the compounds are screened using high-throughput screening assays. Such screening methods are routine in the art and can be performed by one of ordinary skill without undue experimentation.

IV. Nucleic Acid Molecules Encoding ApoD or an Active Variant Thereof

The ApoD polypeptide, or an active variant thereof, can be obtained by expression of a nucleic acid molecule. Thus, nucleic acid molecules encoding polypeptides containing an ApoD polypeptide, or an active variant thereof, are considered within the scope of the invention. Just as an ApoD polypeptide, or an active variant thereof, can be described in terms of their identity with a wild-type ApoD polypeptide, the nucleic acid molecules encoding them will necessarily have a certain identity with those that encode wild-type ApoD. For example, the nucleic acid molecule encoding an active ApoD variant can be at least about 50%, for example, at least about 65%, at least about 75%, at least about 85%, or at least about 95% (e.g., 99%) identical to the nucleic acid encoding wild-type mature ApoD (e.g., SEQ ID NO: 2).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an anti sense strand).

The nucleic acid molecules are not limited to sequences that encode polypeptides; some or all of the non-coding sequences that lie upstream or downstream from a coding sequence (e.g., the coding sequence of ApoD) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules of the invention can include fragments not found as such in the natural state. Thus, the invention encompasses recombinant molecules, such as those in which a nucleic acid sequence (for example, a sequence encoding ApoD, or an active variant thereof) is incorporated into a vector (e.g., a plasmid or viral vector) or into the genome of a heterologous cell (or the genome of a homologous cell, at a position other than the natural chromosomal location).

ApoD, or an active variant thereof, of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into ApoD-encoding DNA obtained from any biological cell, such as the cell of a mammal. Thus, the nucleic acids of the invention (and the polypeptides they encode) can be those of a mouse, rat, guinea pig, cow, sheep, horse, pig, rabbit, monkey, baboon, dog, or cat. Typically, the nucleic acid molecules will be those of a human.

V. Protein Production

The nucleic acid molecules described above can be contained within a vector that is capable of directing their expression in, for example, a cell that has been transduced with the vector. Accordingly, in addition to ApoD, or an active variant thereof, expression vectors containing a nucleic acid molecule encoding an ApoD polypeptide, or an active variant thereof, and cells transfected with these vectors are among the preferred embodiments.

Vectors suitable for use in the present invention include T7-based vectors for use in bacteria (see, for example, Rosenberg et al., *Gene* 56:125, 1987), the pMSXND expression vector for use in mammalian cells (Lee and Nathans, *J. Biol. Chem.* 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body.

Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (nee') gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes an ApoD polypeptide, or an active variant thereof, are also features of the invention. A cell of the invention is a transfected cell, i.e., a cell into which a nucleic acid molecule, for example a nucleic acid molecule encoding an ApoD polypeptide, or an active variant thereof, has been introduced by means of recombinant DNA techniques. The progeny of such a cell are also considered within the scope of the invention.

The precise components of the expression system are not critical. For example, an ApoD polypeptide, or an active variant thereof, can be produced in a prokaryotic host, such as the bacterium *E. coli*, or in a eukaryotic host, such as an insect cell (e.g., an Sf21 cell), or mammalian cells (e.g., CHO cells, COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (*Cloning Vectors: A Laboratory Manual*, 1985 Suppl. 1987).

Cell translation systems can also be used to produce ApoD, or an active variant thereof, as is well known in the art. For such purposes, the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

The expressed polypeptides can be purified from the expression system using routine biochemical procedures, and can be used, e.g., as therapeutic agents, as described herein.

Proteins of the invention can also be produced by chemical synthesis (e.g., by the methods described in Solid Phase Peptide Synthesis, 2nd Edition, The Pierce Chemical Co., Rockford, Ill. (1984)). Modifications to the protein can also be produced by chemical synthesis.

The purified proteins are preferably at least 85% pure, or preferably at least 95% pure, and most preferably at least 98% pure. Regardless of the exact numerical value of the purity, the protein is sufficiently pure for use as a pharmaceutical product.

VI. In Vitro Assays

The efficacy of candidate active ApoD variants in, e.g., protecting tissue (e.g., heart tissue) from ischemic damage, can be readily tested using various in vitro assays. Preferably, the assays are high throughput assays that allow for screening of more than one candidate active ApoD variant simultaneously.

In some embodiments, the cardioprotective effects of a candidate active ApoD variant can be determined in cell-based hypoxia/reoxygenation assays, as described in, e.g., Example 4. The assay involves treating a sample of cultured cells (e.g., primary adult or neonatal cardiomyocytes or cell lines, such as HL-1 mouse cardiomyocytes, and the like) in the absence or presence of wild-type ApoD, a candidate active ApoD variant, and a control (e.g., BSA), followed by subjecting the cells to hypoxia (95% $N_2$/5% $CO_2$) in a hypoxia chamber. After a predetermined duration, cells are then cultured in an oxygen containing atmosphere (e.g., 95% air/5% $CO_2$). This is then followed by a determination of cell viability and/or number using standard commercially available reagents (CellTiter Blue reagent (Promega) or routine methods in the art (e.g., trypan blue staining). A candidate ApoD variant is considered an active ApoD variant if it retains the ability to protect cultured cells from cell death relative to control. In some embodiments, an active ApoD variant may have a lower, equal, or greater protective effect than wild-type ApoD. Amounts of ApoD protein to add to cells and hypoxia/reoxygenation conditions can be readily determined by one of ordinary skill without undue experimentation. In some embodiments, an active ApoD variant retains at least 30%, such as at least 40%, at least 50%, at least 60%, at least 70%, at least 80%, at least 85%, at least 90%, at least 95%, or 100% of the protective activity of wild-type ApoD. In other embodiments, an active ApoD variant has an protective activity up to 5%, up to 10%, up to 20%, up to 30%, up to 40%, up to 50%, up to 60%, up to 70%, up to 80%, up to 90%, up to 100%, up to 150%, or up to 200% or greater than that of wild-type ApoD. In some embodiments, active ApoD variants will be tested for activity in the cell-based hypoxia/reoxygenation assay described above, and followed by in vivo confirmation using the animal models described infra (e.g., the coronary ligation/infarction model).

In other embodiments, the antioxidant activity of an active ApoD candidate can be determined using standard antioxidant assays (e.g., the 2,2'-azino-bis(3-ethylbenzthiazoline-6-sulfonic acid) diammonium salt (ABTS) radical-cation-forming chromogenic reaction, as described in Example 5 (28, 29), diphenylpicrylhydrazyl assays, oxygen radical absorbance capacity assays, and ferric reducing ability of plasma assays) or commercially available kits (e.g., Antioxidant Assay by from IBL International, OxiSelect™ Oxygen Radical Antioxidant Capacity Activity Assay from Cell Biolabs, Inc., and the Antioxidant Assay Kit from Sigma). BSA can be used as a negative control and Trolox ((±)-6-hydroxyl-2,5,7,8-tetramethylchromane-2-carboxylic acid, Sigma) as a positive control in these assays. In some embodiments, an active ApoD variant retains at least 30%, such as at least 40%, at least 50%, at least 60%, at least 70%, at least 80%, at least 85%, at least 90%, at least 95%, or 100% of the antioxidant activity of wild-type apoD. In other embodiments, an active ApoD variant has an antioxidant activity up to 5%, up to 10%, up to 20%, up to 30%, up to 40%, up to 50%, up to 60%, up to 70%, up to 80%, up to 90%, up to 100%, up to 150%, or up to 200% or greater than that of wild-type ApoD.

In some embodiments, the expression (transcript or protein) of ApoD, or an active variant thereof, is determined. Such methods are standard in the art and include, e.g., polymerase chain reaction (PCR), reverse transcriptase polymerase chain reaction (RT-PCR or Q-PCR), Northern blotting, ribonuclease protection assay, methods with DNA chips, methods with transcriptomic chips, methods with oligonucleotide chips, in situ hybridization, enzyme-linked immunosorbent assays (ELISA), immunostaining, and Western blotting.

It should be understood that the assays described herein are exemplary, and that any method known in the art that can serve as a readout for ApoD activity are suitable for use for testing the cardioprotective or antioxidant effects of ApoD, or an active variant thereof.

VII. In Vivo Models

The present invention also encompasses a method of screening for candidate active ApoD variants that treat or reduce tissue damage resulting from ischemia (e.g., myocardial ischemia). Screening can be performed using a non-human mammal (for example, a mouse), and administering to the mammal a candidate ApoD variant, wild-type ApoD, or a control prior to, during, or after an intervention that induces ischemia. The ability of the candidate active ApoD variant to protect tissue from ischemic damage, relative to wild-type ApoD or a control, can then be determined using art-recognized methods.

Various art-recognized animal models exist that recapitulate the symptoms of diseases, disorders, and conditions associated with ischemia (e.g., ischemia in the heart, brain, kidney, bowel, liver, skeletal muscle, and skin), and are suitable for use in testing the efficacy of candidate ApoD active variants, as described below.

Relevant models of myocardial infarction include those that are well known in the art, e.g., the induction of myocardial ischemia by coronary artery ligation followed by reperfusion (as described in the Examples), cauterization, cryo-injury, balloon occlusion, and pharmacologically (e.g., with isoproterenol, adriamycin, and ergonovine). Such models are described in, e.g., Ou et al., *The Open Cardiovascular Medicine Journal* 2010; 4:231-9. Other animal models include transgenic mouse models, such as the scavenger receptor class BI (SR-BI) and apolipoprotein E (ApoE) double knockout mice, SR-BI$^{-/-}$/hypoE mice (knockout of SR-BI and reduced expression of ApoE), PDZK1$^{-/-}$/ApoE$^{-/-}$ mice, and PDZK1$^{-/-}$/hypoE mice as disclosed in U.S. Pat. No. 7,514,592, herein incorporated by reference.

The efficacy of ApoD, or candidate active variants thereof, can be determined by taking baseline measurements and comparing the state of myocardial tissue damage before and after administration of the ApoD, or candidate active variant thereof. For example, commercially available kits can be used to measure blood concentrations of cardiac enzymes, such as troponin T (Roche Diagnostics), creatine kinase, serum glutamic oxalacetic transaminase (SGOT), and lactate dehydrogenase isoenzyme 1 (Paragon); hearts can be removed after perfusion and staining sections with hematoxylin and eosin (Metzler et al., *Cardiovascular Res* 2001; 49:399-407); tissue damage can be examined using the Zingarelli Damage Scoring System (Zingarelli et al., *Circ Res* 1998; 83:85-94); areas at risk and infarction size can be determined with Evans Blue and TTC-staining; the state of myocardial tissue can be examined using transthoracal and transesophageal echocardiography (Ramani et al., *J Am Soc Echocardiogr* 2004; 17:649-53) and single photon emission computed tomography; and magnetic resonance imaging can be used to assess heart function (Chacko et al., *Am J Physiol* 2000; 279:H2218-24). Such methods are reviewed in, e.g., Conci et al., *J Kardiol* 2006; 13:239-44. Other suitable methods include electron microscopy, echocardiography, EKG, and angiograms.

For stroke models, cerebral ischemia can be induced globally or focally by, e.g., cardiac arrest, neck cuff, cephalic artery occlusion, hemorrhage, intracranial hypertension, reperfusion, intraluminal filament, embolism, middle cerebral artery occlusion, perforating artery occlusion, entothelin 1 injection, spontaneous brain infarction (in spontaneously hypertensive rats), bilateral coronary artery occlusion, common carotid artery occlusion, four-vessel occlusion, unilateral artery occlusion, macrosphere embolization, microsphere embolization, and photothrombosis. Such models are described in, e.g., Casals et al., *Comp Med* 2011; 61:305-13; Traystman, *ILAR J* 2003; 44:85-95. The extent of cerebral ischemic damage can be quantified using methods well known to those skilled in the art, e.g., evaluating the extent of glial cell and macrophage invasion into the area of injury, which have significantly greater numbers of peripheral-type benzodiazepine receptor (w3) binding sites compared to neurons. Binding assays can be used to detect the presence of w3 binding sites (see, e.g., Gotti et al., *Brain Res* 1990; 522:290-307). Other assays include myeloperoxidase activity assays and histologic verification.

Hindlimb ischemia can be used as a model of peripheral arterial occlusive disease. The procedure involves ligating and excising the femoral artery and its side branches. Tissue damage can be assessed by, e.g., measuring blood flow (laser Doppler flowmetry), histological measurements of angiogenesis, and a functional analysis of ischemic limbs. Such models are described in, e.g., Madeddu et al., *Vascular Pharmacology* 2006; 45:281-301 and Waters et al., *J Appl Physiol* 2004; 97:773-80).

Relevant animal models for cutaneous ischemia are described in, e.g., Wong et al. (*J Biomedicine and Biotechnology* 2011, Article ID 969618). Exemplary models include the ischemic skin flap model and the pressure ulcer model (Wassermann et al., *Wound Repair and Regeneration* 2009; 17:480-4).

Renal ischemia can be induced in animals by renal clamping as described in, e.g., Kennedy et al., *Nephrology* 2008; 13:390-6. Intestinal ischemia can be induced in animals by superior mesenteric artery occlusion as described in, e.g., Megison et al., *J Surg Res* 1990; 49:168-73. Skeletal muscle ischemia can be induced by, e.g., lower limb ischemia as disclosed in, e.g., Petrasek et al., *J Invest Surg* 1994; 7:27-38; Vignaud et al., *J Biomedicine and Biotechnology* 2010; Article ID 724914. Hepatic ischemia can be induced by, e.g., clamping the hepatic artery and portal vein, as described in, e.g., Abe et al. *Free Radic Biol Med* 2009; 46:1-7.

The efficacy of ApoD, or candidate active variants thereof, in the above models can be determined using art-recognized methods for assessing the function of the relevant tissue of interest (i.e., tissue susceptible to damage by ischemia) or histologically.

VIII. Combination Therapy

ApoD, or a variant thereof, can be used in conjunction with one or more conventional treatments, such as the administration of various pharmaceutical agents and surgical procedures.

In some embodiments, the methods of the present invention include combination therapy with medication known it the art to be useful for the treatment for cardiovascular disease or disorder. Exemplary drugs for use in combination with ApoD, or an active variant thereof, include, but are not limited to, angiotensin-converting enzyme (ACE) inhibitors (e.g., enalapril, lisinopril, and captopril), angiotensin II (A-TO receptor blockers (e.g., losartan and valsartan), diuretics (e.g., bumetanide, furosemide, and spironolactone), digoxin, beta blockers, nesiritide, cholestyramine, colestipol, nicotinic acid, gemfibrozil, probucol, atorvastatin, lovastatin, aspirin, ticlopidine, clopidogrel or anti-coagulants. Combination therapy may also include inhibitors of cardiovascular disease and disorders, including, but not limited to, inhibitors of smooth muscle proliferation, inhibitors of DP1 and/or DP2 receptor, and inhibitors of MAP Kinase.

In some embodiments, the methods of the present invention involve combination therapy with one or more therapeutic agents known to increase angiogenesis (e.g., myocardial angiogenesis), for example, in animal models of ischemia (e.g., myocardial ischemia). Exemplary angiogenesis-inducing agents include, but are not limited to, fibroblast growth factors (e.g., FGF1, FGF2, and FGF5), vascular endothelial growth factors (VEGF) and active fragments thereof (e.g., $VEGF_{165}$), hypoxia inducible factor (HIF-1), platelet-derived growth factors (PDGF1, PDGF2), developmental embryonic locus (DEL) 1, angiopoietins, hepatocyte growth factor (HGF), monocyte chemoattractant protein (MCP-1), endothelial nitric oxide synthase (eNOS), and inducible nitric oxide synthase (iNOS). Such agents are described in, e.g., U.S. Pat. No. 6,759,386 and US 2002/0172663.

In some embodiments, the methods of the present invention can be carried out in conjunction with the injection, implantation, and/or attachment of cultured three dimensional tissue to prevent and/or reduce tissue thinning associated with tissue remodeling in ischemic tissue, as described in, e.g., U.S. Patent Application No. 2012/0276062.

In some embodiments, the methods of the present invention can be practiced before, during, or after a surgical procedure, such as angioplasty, single CABG, and/or multiple CABG. ApoD, or an active variant thereof, can also be used in conjunction with devices used to treat heart disease including heart pumps, endovascular stents, endovascular stent grafts, left ventricular assist devices (LVADs), biventricular cardiac pacemakers, artificial hearts, and enhanced external counterpulsation (EECP).

IX. Compositions and Methods of Administration

The invention provides for pharmaceutical compositions comprising ApoD, or an active variant thereof, and a carrier, e.g., a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

In certain embodiments, acceptable formulation materials preferably are nontoxic to recipients at the dosages and concentrations employed. In some embodiments, the route of administration of the pharmaceutical composition is in accord with known methods, e.g., orally, through injection by intravenous, intraperitoneal, intracerebral (intra-parenchymal), intracerebroventricular, intramuscular, subcutaneously, intradermal, intra-ocular, intraarterial, intraportal, or intralesional routes; by sustained release systems or by implantation devices. In some embodiments, the route of administration is, e.g., myocardial, intrapericardial, endomyocardial, and intracoronary. A unique form of parenteral administration is via direct access to the coronary circulation, added to cardioplegia solutions routinely used during cardiac surgery. Such delivery can follow an antegrade route (via the aortic root into the coronary arteries) and/or a retrograde route (via the coronary sinus, great heart vein). In certain embodiments, the compositions can be administered by bolus injection or continuously by infusion, or by implantation device. In certain embodiments, individual elements of the combination therapy may be administered by different routes.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (e.g., glycine, glutamine, asparagine, arginine or lysine); antimicrobials; antioxidants (e.g., ascorbic acid, sodium sulfite or sodium hydrogen-sulfite); buffers (e.g., borate, bicarbonate, Tris-HCl, citrates, phosphates or other organic acids); bulking agents (e.g., mannitol or glycine); chelating agents (e.g., ethylenediamine tetraacetic acid (EDTA)); complexing agents (e.g., caffeine, polyvinylpyrrolidone, beta-cyclodextrin or hydroxypropyl-beta-cyclodextrin); fillers; monosaccharides; disaccharides; and other carbohydrates (e.g., glucose, mannose or dextrins); proteins (e.g., serum albumin, gelatin or immunoglobulins); coloring, flavoring and diluting agents; emulsifying agents; hydrophilic polymers (e.g., polyvinylpyrrolidone); low molecular weight polypeptides; salt-forming counterions (e.g., sodium); preservatives (e.g., benzalkonium chloride, benzoic acid, salicylic acid, thimerosal, phenethyl alcohol, methylparaben, propylparaben, chlorhexidine, sorbic acid or hydrogen peroxide); solvents (e.g., glycerin, propylene glycol or polyethylene glycol); sugar alcohols (e.g., mannitol or sorbitol); suspending agents; surfactants or wetting agents (e.g., pluronics, PEG, sorbitan esters, polysorbates such as polysorbate 20, polysorbate 80, triton, tromethamine, lecithin, cholesterol, tyloxapal); stability enhancing agents (e.g., sucrose or sorbitol); tonicity enhancing agents (e.g., alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the ApoD polypeptide, or variant thereof, or nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the ApoD polypeptide, or variant thereof, or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds (ApoD, or an active variant thereof, or nucleic acids) can also be prepared in the form of suppositories (e.g., with conventional suppository bases such as cocoa butter and other glycerides) or retention enemas for rectal delivery.

The compounds (ApoD, or an active variant thereof, or nucleic acids) can also be administered by transfection or infection using methods known in the art, including but not limited to the methods described in McCaffrey et al. (*Nature* 418:6893, 2002), Xia et al. (*Nature Biotechnol.* 20:1006-1010, 2002), or Putnam (*Am. J. Health Syst. Pharm.* 53:151-160, 1996, erratum at *Am. J. Health Syst. Pharm.* 53:325, 1996).

In one embodiment, the ApoD polypeptide, or variant thereof, or nucleic acids are prepared with carriers that will protect the ApoD polypeptide, or variant thereof, against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

Dosage, toxicity, and therapeutic efficacy of ApoD, or an active variant thereof, or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

X. Methods of Prophylaxis/Treatment

In one aspect, the present invention involves the use of ApoD, or an active variant thereof, for the treatment or reduction of tissue damage resulting from ischemia (e.g., myocardial ischemia) in subjects in need thereof (ischemic injury exists) or at risk of developing tissue damage from ischemia. Accordingly, in some embodiments, ApoD, or an active variant thereof, can be administered before ischemic injury exists (e.g., preoperatively or in subjects at risk of ischemic damage, such as genetically predisposed), during the development of ischemic injury (e.g., during surgery), or after ischemic injury (e.g., postoperatively, or after myocardial infarction).

Examples of disease states for which the method can be applied to treat or reduce ischemic injury include, for example, coronary artery disease, myocardial infarctions, Prinzmetal angina, cardiac rupture, congestive heart failure, pulmonary infarctions, peripheral vascular occlusive disease, stroke, cerebral infarction, vascular occlusion, pre-natal or post-natal oxygen deprivation, ischemic wounds, trauma, including surgery and radiotherapy, chronic obstructive pulmonary disease, emphysema, adult respiratory distress syndrome, septic shock, sickle cell crisis, dysrhythmias, nitrogen narcosis and neurological deficits caused by heart-lung bypass procedures, and the like. Efficacy of the administered composition can be monitored by the absence or a decrease in severity of ischemic injury (e.g., myocardial ischemic injury) using standard methodology. For example, in myocardial ischemic injury, cardiac enzyme leakage, cardiac contractile protein leakage, left and right cardiac ventricular cavity pressures, arrhythmias and S-T segment elevation can be assessed to determine the efficacy of the administered composition.

For therapeutic applications, compositions including ApoD, or an active variant thereof, are administered to a subject suspected of having, or already having such a ischemic/reperfusion injury (e.g., from myocardial ischemia) in an amount effective to cure, or at least partially arrest, the symptoms of the injury (biochemical, histologic and/or physiological). An amount adequate to accomplish therapeutic or prophylactic treatment is defined as a therapeutically or prophylactically-effective dose or as an effective dose. The compositions can be administered one or more times per day to one or more times per week; including once every other day; until a desired effect has been achieved.

When treating an existing I/R injury, the composition is administered after surgery or post-reperfusion. In such cases, the dosing scheme is designed to produce and maintain an effective amount of ApoD, or an active variant thereof, in the bloodstream of the patient. A clinician can adjust the dosage of ApoD, or an active variant thereof, the frequency of administration, and the duration of treatment accordingly. A composition including ApoD, or an active variant thereof, can be administered at any time following, e.g., reperfusion of the ischemic myocardium, e.g., seconds, minutes, days, or weeks, for example, daily in single or divided doses. Thus, ApoD may be administered after surgery or reperfusion of the ischemic myocardium or post-angioplasty, coronary artery bypass surgery, or thrombolytic therapy and continuing daily for a predetermined period.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of ApoD polypeptide or a variant thereof, can include a single treatment or can include a series of treatments.

For prophylactic applications, compositions or medicaments are administered to a subject susceptible to, or otherwise at risk of, having or developing ischemic injury (e.g, myocardial ischemia/reperfusion injury—subjects at risk for heart attack, stroke, myocardial infarction, etc.) in an amount sufficient to eliminate or reduce the risk, lessen the severity, or delay the outset of the injury, including biochemical, histologic and/or physiologic symptoms of the injury. In some embodiments, ApoD, or an active variant thereof, is administered to a subject concurrently with surgery to prevent myocardial ischemic/reperfusion injury associated with cardiac surgery or transplantation. In other embodiments, ApoD, or an active variant thereof, is administered prior to (on a daily basis) surgery, e.g., angioplasty, coronary bypass surgery, or thrombolytic therapy, and the resulting reperfusion of the ischemic myocardium. Dosing of ApoD, or an active variant thereof, is controlled to produce and maintain an effective amount of ApoD, or an active variant thereof, in the bloodstream of the patient during or before the reperfusion event.

Clinical indicators of coronary artery disease are described in, e.g., U.S. Pat. No. 6,759,386, and include, but are not limited to, levels of creatine phosphokinase-MB (CPK-MB), electrocardiogram tracings, chest pain, frequency and intensity of anginal symptoms, myocardial perfusion, electrocardiogram tracings, scores on quantitative angina scales, and angiography.

A subject at risk of coronary artery disease may present with one or more of the following risk factors: previous cardiovascular disease, old age, tobacco smoking, hyperlipidemia, low HDL cholesterol levels, type II diabetes/impaired glucose tolerance (IGT), obesity, chronic kidney disease, alcohol consumption, essential hypertension (i.e., hypertension without discoverable organic cause), or a family history of coronary artery disease. Such subjects may be identified as having elevated fasting blood glucose, elevated HgbAlc, elevated C-peptide, elevated fasting total cholesterol, elevated fasting LDL-cholesterol, decreased fasting HDL-cholesterol, a high LDL/HDL ratio, elevated fasting triglycerides, elevated fasting free fatty acid concentration, elevated body weight, elevated systolic blood pressure, and elevated diastolic blood pressure. Additional factors that predict the risk of coronary heart disease include levels of serum inflammatory markers, such as C-reactive protein (CRP), serum amyloid A, fibrinogen, interleukin-6, tissue necrosis factor-alpha, soluble vascular cell adhesion molecules (sVCAM), soluble intervascular adhesion molecules (sICAM), E-selectin, matrix metalloprotease type-1, matrix metalloprotease type-2, matrix metalloprotease type-3, and matrix metalloprotease type-9 (see, e.g., Stein, *Am J Cardiol*, 2001; 87:21A-26A). Subjects at risk of coronary artery disease may also be genetically susceptible to developing the disorder. Genetic mutations or polymorphisms shown to modify CAD risk include those disclosed in, e.g., "Genetic risk for coronary artery disease" by the International Task Force for Prevention of Coronary Heart Disease (accessible at www.chd-taskforce.de/chd_prevention_slidekits), Morrison et al., *American Journal of Epidemiology* 2007; 166:

28-35, and Peden et al., *Hum Mol Genet* 2011; 20:R198-R205. Other risk factors for developing coronary heart disease are disclosed in, e.g., Helfand et al., *Annals of Internal Medicine* 2009; 151:496-510.

For both therapeutic and prophylactic treatments, the clinician can titer the dosage and modify the route of administration to obtain the optimal therapeutic effect. One skilled in the art will appreciate that the appropriate dosage levels, according to certain embodiments, will thus vary depending, in part, upon the molecule(s) delivered (e.g., for combination therapy), the route of administration, and the size (body weight, body surface or organ size) and/or condition (the age and general health) of the subject. These parameters can be readily determined by a qualified clinician. Generally, the dose sufficient to treat or ameliorate symptoms or signs of disease, or for prophylaxis against a disease or disorder, is a dose that does not produce unacceptable toxicity to the subject.

The extent of improvement or inhibition of ischemic tissue damage in the methods of the invention can be monitored using routine methods, such as ultrasound, magnetic resonance imaging, CAT scan, echo (e.g., cardiac echo), EEG, EKG, EMG, or blood tests.

XI. Kits

A kit can include ApoD, or an active variant thereof, and optionally one or more therapeutic agents (e.g., VEGF, FGF), and instructions for use. The kits may comprise, in a suitable container, ApoD, or an active variant thereof, and optionally one or more therapeutic agents, one or more controls, and various buffers, reagents, enzymes and other standard ingredients well known in the art.

The container can include at least one vial, well, test tube, flask, bottle, syringe, or other container means, into which ApoD, or an active variant thereof, and optionally one or more therapeutic agents, may be placed, and in some instances, suitably aliquoted. Where an additional component is provided, the kit can contain additional containers into which this component may be placed. The kits can also include a means for containing ApoD, or an active variant thereof, and optionally one or more therapeutic agents, and any other reagent containers in close confinement for commercial sale. Such containers may include injection or blow-molded plastic containers into which the desired vials are retained. Containers and/or kits can include labeling with instructions for use and/or warnings.

All publications, patents, and patent applications cited herein, whether supra or infra, are hereby incorporated by reference in their entirety.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used, but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992).

Materials and Methods

Materials

Rabbit polyclonal anti-mouse ApoD antibody (cat No. NBP1-40025) was purchased from Novus Biologicals (Littleton, Colo.). $SR-BI^{-/-}$ $apoE^{-/-}$ (dKO) mice (strain 2, mixed C57BL/6/SV129/BALB/c background) and control $SR-BI^{-/-}$ $apoE^{-/-}$ (Het) mice (strain 2 (on the same mixed C57BL/6/SV129/BALB/c background)) were generated and maintained as previously described (Trigatti et al., *PNAS* 1999; 96:9322-7; Braun et al., *Circ Res* 2002; 90:270-6; Karackattu et al., *Arterioscler Thromb Vasc Biol* 2005; 25:803-8). ApoD KO mice backcrossed>10 times into the C57BL/6 background (Hildebrand et al., *Hear Res* 2005; 200:102-14) were generated and initially characterized as described below. Wild-type C57BL/6 control mice are commercially available from the Jackson Laboratory and were housed in the same room as ApoD KO mice at least one week before the experiment. Experiments using animals were performed in accordance with the guidelines of the Committee on Animal Care at the Massachusetts Institute of Technology. Adult and 1 to 2 day old neonatal Wistar rats were purchased from Charles River Laboratories.

Generation and Characterization of ApoD KO Mice

The mouse ApoD gene is on chromosome 16 and contains 5 exons spanning 18.4 kb. The targeting construct was designed to delete the second exon that includes the start of translation and the signal peptide needed for protein secretion. An 885 bp short arm was cloned from strain 129 genomic DNA by PCR using the primers AATGCAATC-CTGATTCTGCTT (SEQ ID NO: 5) and GCTCAGAGC-CTTGATACC (SEQ ID NO: 6). The product ends 71 bp 5' to the EcoRI site that is upstream of exon II. A 6.7 kb long arm XbaI fragment was subcloned from a 129 strain mouse genomic Bac clone. The long and short arms were subcloned flanking the pGKneo polyA+ cassette, which was in the same orientation as the ApoD gene. The targeting construct was electroporated into R1 embryonic stem (ES) cells, and neo resistant colonies were selected as previously described (Weng et al., *PNAS* 1996; 93:14788-94). Homologous recombination was detected by PCR of genomic DNA prepared from ES cell clones. PCR for the knockout allele used a sense primer located 5' to the short arm AAGTTG-GACCTACACATCAGCTGAC (SEQ ID NO: 7) and an antisense primer in the neo cassette TGCGAGGCCAGAG-GCCACTTGTGTAGC (SEQ ID NOT: 8) yielding an ~1100 bp product that cannot be generated from the targeting vector by random integration. The wild-type allele was detected using the same sense primer and an anitsense primer in exon 2 CTTTTTCACGTCAAAATTCTCTTG-CAC (SEQ ID NO: 9) that yields an ~1350 bp product. One ES cell line with homologous recombination of the targeting vector was used for C57BL/6 blastocyst microinjection as previously described (Weng et al., 1996). Male mice, 90 to 100% chimerism as detected by coat color, were bred to C57BL/6 females and germ line transmission was obtained. The mice that were the subjects of the current study were bred back to the C57BL/6 background for a minimum of 10 generations. For the generation and initial characterization of these mice, these animals were fed rodent chow (Harlan Teklad 2018). The ApoD knockout (KO) mice were initially generated and characterized in the laboratory of J. Breslow at the Rockefeller University following protocols approved by the Rockefeller Institutional Animal Care and Use Committee. ApoD KO mice were also maintained at the Cleveland Clinic following protocols approved by the Cleveland Clinic Institutional Animal Care and Use Committee.

Histological Analysis

The dKO and Het mice were anesthetized and perfused with PBS and 4% PFA and their hearts and proximal aortas were harvested. The tissues were embedded in paraffin and cut into 5 µm transverse sections, which were stained with Movat pentachrome connective tissue stain. Thus, localized areas of proteoglycan (bluish-green) and collagen (yellow) were used to recognize fibrotic tissue.

RNA Isolation

Whole hearts (including atria) were harvested and frozen and then ground in Trizol (Invitrogen). Total RNA was extracted with either chloroform for microarray analysis or 1-bromo-3-chloropropane (BCP) for qRT-PCR analysis. The extracted RNA was then precipitated in ethanol (microarray) or isopropanol (qRT-PCR) and dissolved in DEPC-treated water prior to analysis.

Microarray Analysis

RNAs from each heart harvested at either 21, 31 or 43 days of age (n=9-12 for each genotype and age) were independently processed and analyzed using MG_U74Av2 microarray (Affymetrix) gene chips (1 heart/chip) and standard methods (Nutt et al., *Cancer Res* 2003; 63:1602-7). The raw data in the form of CEL files have been uploaded to Gene Expression Omnibus (GEO) (www.ncbi.nlm.nih.gov/geo/). Data were processed and quality control metrics were calculated using the Affy library in Bioconductor (Gautier et al., *Bioinformatics* 2004; 20:307-15) along with custom R (R Development Core Team., "R: A language and environment for statistical computing. R Foundation for Statistical Computing, Vienna, Austria. ISBN 3-900051-07-0, www.R-project.org) programs. The GenePattern platform (Reich et al., *Nat Genet* 2006; 38:500-1; Gene Pattern website, www-.broadinstitute.org/cancer/software/genepattern/) was used for differential gene expression analysis between Het and dKO mice, and for heat map generation. The gene expression profiles were normalized using quantile normalization. Data were then threshold to enforce a minimum probe intensity of 20 and a maximum intensity of 20000, and then filtered to retain only those probes that had a minimum fold change (across all types and ages) of 3 and a minimum expression range of 100. Differential markers were identified using the t-test and corrected for multiple testing using FDR (Benjamini et al., *J Royal Statistical Society. Series B (Methodological)* 1995; 289-300). Self-Organizing Map (SOM) clustering of the normalized and filtered data was performed in GenePattern to obtain 5 clusters (with number of clusters being decided based on exploring SOM output with 4-6 clusters). The statistical significance of the SOM clusters was evaluated using the RxC contingency table extension of Fisher's Exact test (Agresti A. *Categorical Data Analysis*, $2^{nd}$ edition. New York, USA: Wiley; 2002; Mehta et al., *ACM Transactions on Mathematical Software* 1986; 12:154-61). For each SOM cluster, the test evaluated the statistical significance of the proportion of samples belonging to each type (dKO or Het at 21d, 31d and 43d) compared to the total number of samples present for the corresponding type.

Gel Electrophoresis and Immunoblotting

For immunoblotting, plasma samples (30 µg each, determined using the BCA assay (Pierce)) were fractionated using 15% SDS-PAGE, transferred onto polyvinylidene difluoride (PVDF) membranes and ApoD was visualized using rabbit polyclonal anti-mouse ApoD antibody (1:500) (NOVUS Biologicals) and HRP-conjugated secondary antibodies together with an enhanced chemiluminescence (ECL) plus kit (GE Healthcare) according to the manufacturer's protocol. The relative amounts of ApoD in the plasma of mice were determined using Image J software.

Human ApoD Purification, Dialysis and Heat Denaturation

ApoD was purified from human breast cyst fluid following the method of Haagensen et al. (Haagensen et al., *J Natl Cancer Inst* 1979; 62:239-47; Pearlman et al., *J Endocrinol* 1977; 75:19P-20P; Kesner et al., *Cancer Res* 1988; 48:6379-83). In brief, ~13 mL of human breast cyst fluid was centrifuged at 125,000×g for 2 hours. The supernatant was filtered (0.22 µm PVDF filter), and 1 mL of the filtrate was diluted 4.5-fold with 0.15 M $NaH_2PO_4$ buffer, pH 4.5 (buffer A), and buffer exchanged with buffer A using Sephadex G50 medium (GE Healthcare) chromatography (Haagensen et al., *Clin Chem* 1978; 24:135-7). The hydroxyl apatite column was prepared using 21 g of hydroxyl apatite (Fast flow) (Calbiochem) swollen in 0.15 M $NaH_2PO_4$ buffer (pH 4.5). The buffer exchanged breast cyst fluid (approximately 6.5 mL) was then applied to the hydroxyl apatite column (21 g pre-equilibrated with buffer A). The column was washed with 30 mL of buffer A and then the ApoD was eluted from the column with a 3:2 mixture of buffer A and 0.15 M $Na_2HPO_4$, pH 6.5. Fractions containing essentially homogenously pure ApoD determined by SDS-PAGE were pooled (~9 mL) and then subjected to buffer exchange chromatography with phosphate buffered saline (PBS). Then the sample was concentrated with an Amicon filter (Ultracel 10 k, Millipore) and was sterilized with a 0.22 µm filter. The purity of ApoD protein was evaluated by SDS-PAGE as described above. This analysis showed a single band at ~25 kDa that was identical to a previously purified ApoD standard from breast cyst fluid (Pearlman et al., *JBC* 1973; 248:5736-41). The concentration of purified ApoD was determined either by amino acid analysis or absorbance at 280 nm (1.0 $OD_{280}$ unit=0.64 mg/mL, based on amino acid analysis-determined reference).

To remove any poorly bound small molecule ligands, ApoD (~100 µl, 2.5-3.0 mg/mL) was extensively dialyzed (Slide-A-Lyzer® Mini Dialysis Unit (10,000 MWCO); Pierce) against nitrogen saturated PBS as follows: four changes of a 10,000-fold excess of PBS dialysate, 2 hours each followed by a single overnight dialysis against a 30,000-fold excess of PBS. To heat denature the protein, ApoD was incubated at 100° C. for 5 or 8 min in a C1000 Thermal Cycler (Bio-Rad). The effects of heating ApoD on its activities in both the antioxidant assay and the cardiomyocyte assay were similar for 5 and 8 minutes of heating. There was no change in protein concentration ($OD_{280}$) after 5 minutes of heating.

Antioxidant Assay

The 2,2'-azino-bis(3-ethylbenzthiazoline-6-sulfonic acid) diammonium salt (ABTS) radical-cation-forming chromogenic reaction, a standard assay for antioxidants originally described by Miller et al (Miller et al., *Free Radic Res* 1997; 26:195-9; Yu et al., *Anal Biochem* 1999; 275:217-23), was used to assess the potential antioxidant capacity of native, dialyzed or heat denatured ApoD, with BSA used as a negative control. The reaction is catalyzed by myoglobin and initiated by urea hydrogen peroxide. Trolox ((±)-6- hydroxyl-2,5,7,8-tetramethylchromane-2-carboxylic acid, Sigma), a vitamin E derivative, was used as a positive control and standard against which the proteins were compared (Yu et al., 1999). In brief, a FAST/ABTS solution was prepared by adding 70 µl of 10 mg/mL ABTS solution (prepared by adding one tablet of ABTS (Sigma) to 1 mL of water) to 1 mL of 0.53 mg/mL urea hydrogen peroxide, 0.067 M phosphate citrate buffer, pH 5 (prepared by adding one tablet of urea hydrogen peroxide/phosphate-citrate from the SigmaFAST OPD tablet set (Sigma) to 15 mL of water). Reactions in the wells of 96 well plates were initiated by adding 40 µL of equine heart myoglobin (10 µg/mL in water, Sigma, catalog number M1882), 20 µL of test samples (30 µg/mL) and 120 µL of FAST/ABTS solution. After incubation for 45-60 minutes at room temperature, the extent of reaction was measured in a plate reader at 405 nm. Antioxidant capacity is presented as Trolox equivalents. The kinetics of Trolox and ApoD inhibition of ABTS oxidation in this assay differed (not shown), suggesting that their mechanisms of inhibition are not identical.

Isolation of Primary Rat Cardiomyocytes

Neonatal rat ventricular myocytes (NRVMs) were isolated as previously described (Lim et al., JBC 2004; 279: 8290-99; Sadoshima et al., JBC 1992; 267:10551-60; Fisch et al., PNAS 2007; 104:7074-9) from one litter (~10 neonates) of 1 to 2 day old Wistar rat neonates (Charles River Laboratories) with trypsin and collagenase digestion. The isolated NRVMs were incubated for 48 h prior to hypoxia/reoxygenation treatments in DMEM (low glucose) supplemented with 7% FBS, vitamin $B_{12}$, (2 mg/mL), BrdU (31.2 µg/mL), and 100 IU/mL of penicillin and 100 mg/mL of streptomycin (medium A). Adult rat ventricular myocytes (ARVMs) were isolated as previously described (Jain et al., Circ Res 2003; 93:e9-16) from 180 to 200 g male Wistar rats (Charles River Laboratories) with collagenase/hyaluronidase perfusion followed by collagenase/hyaluronidase/Trypsin/DNaseI digestion. The isolated ARVMs were plated into laminin-coated cell culture dishes, and cultured in DMEM (low glucose) supplemented with 100 IU/mL of penicillin and 100 mg/mL of streptomycin (medium B) overnight before the experiment.

Cardiomyocyte Hypoxia/Reoxygenation (H/R)

Cardiomyocytes were plated into either P-35 dishes (ARVM) ($1.0 \times 10^5$ cells/dish) or 96-well plates (NRVMs) ($3.0 \times 10^4$ cells/well), incubated either overnight (ARVM) or for 48 h (NRVM), and then were pre-incubated for 1 h in medium B with or without 100 µg/mL of either human ApoD or BSA. The concentration of ApoD added to the culture media was similar to that observed in human plasma (75-300 µg/mL, or approximately 3-12 µM, 35-37). The pre-incubated cardiomyocytes were then subjected to hypoxic conditions (95% $N_2$ and 5% $CO_2$ atmosphere) for either 24 h (NRVMs) or 16 h (ARVMs) in a modular incubator chamber (Billups-Rothenberg). They were then subjected to reoxygenation conditions (normal atmosphere) for either 6 h (NRVMs) or 8 h (ARVMs). Controls included cells maintained throughout in the normal atmosphere ("without H/R"). At the end of the reoxygenation period, ARVMs in P-35 dishes were assayed by visual inspection for total cell number and viability (trypan blue (0.4%, Sigma, 5-10 min) exclusion). Viability of NRVMs in 96 well plates (n=8 replicates/condition) was determined using the CellTiter Blue reagent (Promega). In each well, 20 µL of CellTiter Blue reagent was added to 100 µL of culture medium, and the cells were incubated ~3 h at 37° C. The fluorescent signals ($560_{Ex}/590_{Em}$) were recorded using a microplate reader. Addition of either ApoD (untreated, dialyzed or boiled) or BSA to the medium of NRVMs slightly improved cell viability of unstressed cells. To account for these small, but significant effects of protein addition to the unstressed cells, the results of the CellTiter Blue viability assay are reported as "H/R induced cell death (%)" calculated as follows:

H/R induced cell death (%)=(1.0−cell viability with H/R÷average cell viability without H/R)×100

Adenovirus-Mediated Gene Transfer

Mouse ApoD cDNA was kindly provided by Dr H. Henry Dong (Rangos Research Center, Children's Hospital of Pittsburgh of University of Pittsburgh Medical Center) (Perdomo et al., J Lipid Res 2010; 51:1298-1311). Adenovirus vectors encoding either mouse ApoD cDNA (Ad-ApoD) or control empty vector (Ad-control) were constructed using the Adeno-X Expression System 1 (Clontech), and virions were isolated and characterized as described previously (Tsukamoto et al., Arterioscler Thromb Vasc Biol 2002; 22:1899-1904). Adenovirus vectors were propagated in HEK293 cells, and purified using a CsCl gradient. The purified adenovirus was dialyzed against 10 mM Tris-HCl (pH 8.0), 2 mM $MgCl_2$, 4% sucrose and sterilized using a 0.22 µm filter (Millipore). Viral titer was determined by measuring tissue culture infectious dose 50 ($TCID_{50}$) using HEK293 cells as described in the product manual for AdEasy vector system (Qbiogene). Adenovirus vectors ($2.5 \times 10^8$ PFU) were injected into mice through the tail vein. The expression of ApoD was assayed by semiquantitative immunoblotting of ApoD in plasma samples drawn 4, 7 and 14 days after injection. The ischemia-reperfusion surgery was performed 4 days after adenovirus injection at which time the plasma levels of ApoD were highest.

Ischemia-Reperfusion Surgery

All surgeries were performed following protocols approved by the MIT Department of Comparative Medicine and the Brigham and Women's Hospital (Boston) according to nationally approved standards of care. Experiments involved either comparisons of 11 week old male wild type C57BL/6 and ApoD KO mice (KO experiments) or comparisons of 9 week old male, wild-type C57BL/6 mice that were injected with either Ad-ApoD or Ad-control viruses (Ad experiments). Ischemia-reperfusion (TIR) was induced in adult mice as described previously (Matsui et al., JBC 2002; 277:22896-901; Mouquet at al., Fundam Clin Pharmacol 2010; 24:469-76; Oikonomopoulos et al., Circ Res 2011; 109:1363-74). In brief, mice were anesthetized either with pentobartital (for KO experiments) or isoflurane (Ad experiments). A sterile suture was placed around the coronary artery 2 mm below the left atrium and passed through a snare. The left coronary artery was ligated through tying of the snare. Proper ligation was confirmed by observing paloring of the LV wall. Ischemia was induced by coronary artery occlusion for 45 minutes (KO experiments) or for 1 hour (Ad experiments) and followed by reperfusion (removal of the snare, suturing the incision). During ischemia, fluorescent polystyrene microspheres (Invitrogen) were injected through left ventricle to permit subsequent quantitation of the area at risk (AAR).

Histological Evaluation of Myocardial Infarction

Twenty four hours after initiating reperfusion, the mice were injected with 1000 units of heparin and euthanized with ~65 mg/Kg body weight pentobarbital injected i.p. The hearts were isolated and arrested at diastole with 3 M KCl. The ventricles were excised and cut into 1 mm thick sections (typically, 5 sections/heart). The sections were stained with 2,3,5-triphenyl tetrazolium chloride (TTC) (1%, Sigma) and fixed with 10% formalin (Sigma). The sections were analyzed under a microscope and images were recorded for subsequent analysis. The infarct area (the white area after TTC staining) and area at risk (the area without fluorescent signal of microspheres) were quantitated from micrographs using Image J software.

Statistics

P<0.05 was considered significant. Except for P values associated with FDR for the microarray analysis (see above), all P values (Student's t-test) and SEM values were calculated using Prism 5 software (GraphPad).

Example 1

SR-BI$^{-/-}$ apoE$^{-/-}$ Mice Exhibit Coronary Arterial Lesions and Myocardial Infarctions in a Temporal Manner SR-BI$^{-/-}$/apoE$^{-/-}$ ('dKO') mice fed a standard chow diet spontaneously develop occlusive, atherosclerotic coronary artery disease (CAD) and heart failure, with a median survival of approximately 6 wk (FIG. 1A) (7, 20). Control SR-BI$^{+/-}$/apoE$^{-/-}$ ('Het') mice do not exhibit signs of CAD or premature death (Braun et al., Circ Res 2002; 90:270-6). One measure of CAD in dKO mice is an increase in the heart (mg)-to-body (g) weight ratio. This ratio was within the normal range (Braun et al., 2002; Zhang et al., Circulation 2005; 111:3457-64; Karackattu et al., Arterioscler Thromb Vasc Biol 2005; 25:803-8) at 21 d, and increased over time in dKO mice (FIG. 1B), indicating the development of heart failure. Histological analysis showed that at 21 d there were no apparent coronary arterial lesions or MIs (FIGS. 1C and 1D, no CAD), whereas at 31 d there were atherosclerotic coronary arterial occlusions and small MIs (FIGS. 1E and 1F, modest disease), and at 43 d there were coronary arterial occlusions and extensive MI (FIGS. 1G and 1H, severe disease when approximately half the dKO mice have died). To determine how disease development influenced gene expression in the hearts of dKO mice at these ages (21 d, 31 d or 43 d) and for each genotype (dKO, Het), microarray analysis was performed on mRNA extracted from the hearts of 9-12 mice (Affymetrix MG_U74Av2 (12488 probes) gene chips (1 heart/chip, 60 hearts analyzed).

Example 2

ApoD Expression is Induced in Hearts of SR-BI$^{-/-}$ apoE$^{-/-}$ Mice

Unsupervised clustering using self-organizing maps was used to cluster the mice into 5 groups that almost perfectly distinguished between hearts from control Het and dKO mice and between hearts of dKO mice at different ages that exhibited different extents of disease progression (FIG. 1). These data suggest that effects of disease progression on cardiac gene expression in the dKO mice are robustly reproducible.

The number of probes exhibiting statistically significant expression differences (false discovery rate (FDR) P value<0.05) between dKO and control Het hearts increased dramatically with age (21 to 43 d)—the number of probes exhibiting >2-fold expression level changes (increased expression/decreased expression) were: 21 d, 18/4; 31 d, 282/118; and 43 d, 791/525. The number of probes at 43 d exhibiting a >6-fold increase in dKO relative to Het hearts was 100, representing 89 independent genes. Many of the genes that increased showed: a) relatively little difference in expression levels compared to the Het control at 21 d, b) a moderate increase in relative expression at 31 d and c) a striking increase at 43 d. Dozens of the genes observed to increase substantially in the dKO hearts have been described previously as being induced in the heart after acute MI (e.g., Tarnavski et al., Physiol Genomics 2004; 16:349-60; NHLBI Program for Genomic Applications, Harvard Medical School. Genomics of Cardiovascular Development, Adaptation, and Remodeling, www.cardiogenomics.org). The two genes having the highest induction of expression were osteopontin ('OPN', also called 'Spp1') with a 416-fold increase and ApoD with a 79-fold increase; their expression levels increased with increasing age (and severity of CAD) in the dKO mice (e.g., see FIG. 2A). Expression of inflammation-associated genes increased and of mitochondrial associated genes, including the transcription factor ERRa (Karamanlidis et al., Circ Res 2010; 106-1541-8), decreased with CAD progression, as expected.

Of the 89 genes whose expression increased >6-fold in dKO relative to Het hearts at 43 d, 81 were induced in mouse hearts between 1 h and 8 wk after surgical coronary artery ligation (Tarnavski et al., 2004; NHLBI Program for Genomic Applications, supra). Thus, it appears that the largest gene expression changes in the dKO hearts are due primarily to the occlusive CAD in these mice. It is unlikely that these changes in expression were due merely to a direct response of the hearts to the dyslipidemia of dKO mice, as there was no dyslipidemia expected in the mice used for the coronary artery ligation study (Cardiogenomics data; Tarnavski et al., 2004; NHLBI Program for Genomic Applications, supra). Some of these 81 genes have been reported to increase in the hearts in other models of CAD or in several tissues after pathologic stress. These include genes encoding matricellular proteins, matrix proteases, TIMPs, and inflammation and fibrosis associated proteins. Eight of the 89 genes that increased >6-fold in the dKO data did not increase in the coronary artery ligation model. Seven of these defined a distinct hierarchical cluster and appear to be related to early erythroid development and presumably are independent of the CAD.

Figure 2:
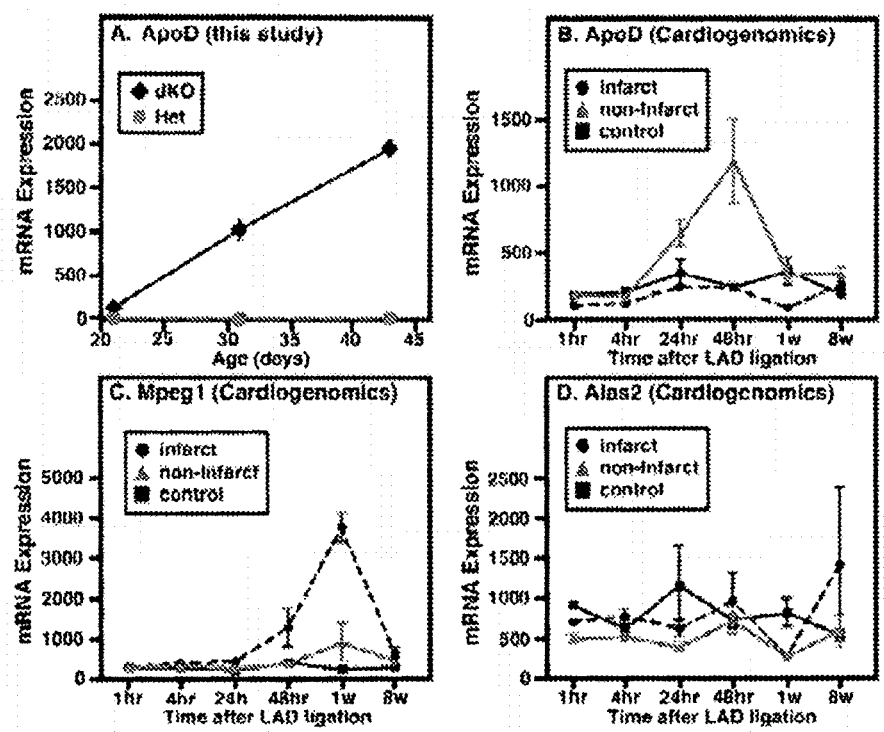
FIG. 2 depicts the temporal mRNA expression of ApoD in heart tissue.

The Cardiogenomics data (Tarnavski et al., 2004; NHLBI Program for Genomic Applications, supra) included samples from control, sham operated hearts, and from hearts taken from both regions that were infarcted and non-infarcted after coronary artery ligation. FIGS. 2B and 2C, respectively, show examples from the Cardiogenomics's time course data of two of these 81 genes that were increased in both the dKO and Cardiogenomics data: ApoD and Mpeg1 (a macrophage expressed gene). Of these 81 genes, 76 showed increased expression in infarcted relative to non-infarcted tissue, the majority of which showed peak expression at 1 wk after ligation (e.g., Mpeg1 in FIG. 2C). Four genes exhibited peak expression levels that were similar in the infarcted and non-infarcted tissue. The time course after coronary artery ligation of increased expression of ApoD was distinctive. Its increased expression was substantially higher in non-infarcted relative to infarcted tissue and occurred relatively soon (48 h) after ligation (FIG. 2B). Indeed, there was little increase in ApoD expression in the infarcted tissue. Given this unique expression pattern, a potential role of ApoD in protecting against CAD was examined.

Example 3

Increased ApoD Expression Protects Against, while Reduced ApoD Expression Exacerbates, In Vivo Myocardial Infarction Given that ApoD was a highly induced gene in SR-BI$^{-/-}$ apoE$^{-/-}$ dKO mice and in non-infarcted tissue relative to infracted tissue after coronary artery ligation, the in vivo the effects of increasing ApoD expression were examined. As an exemplary method for increasing ApoD expression in the animals, ApoD was overexpressed in the liver (a non-damaged tissue in response to the coronary ligation model) by adenovirus (Ad)-mediated infection. Conversely, to examine the effects of loss of ApoD on cardiac tissue damage resulting from myocardial infarction by ischemia/reperfusion (I/R) stress, homozygous genomic knockout ApoD expression was used.

Figure 3:
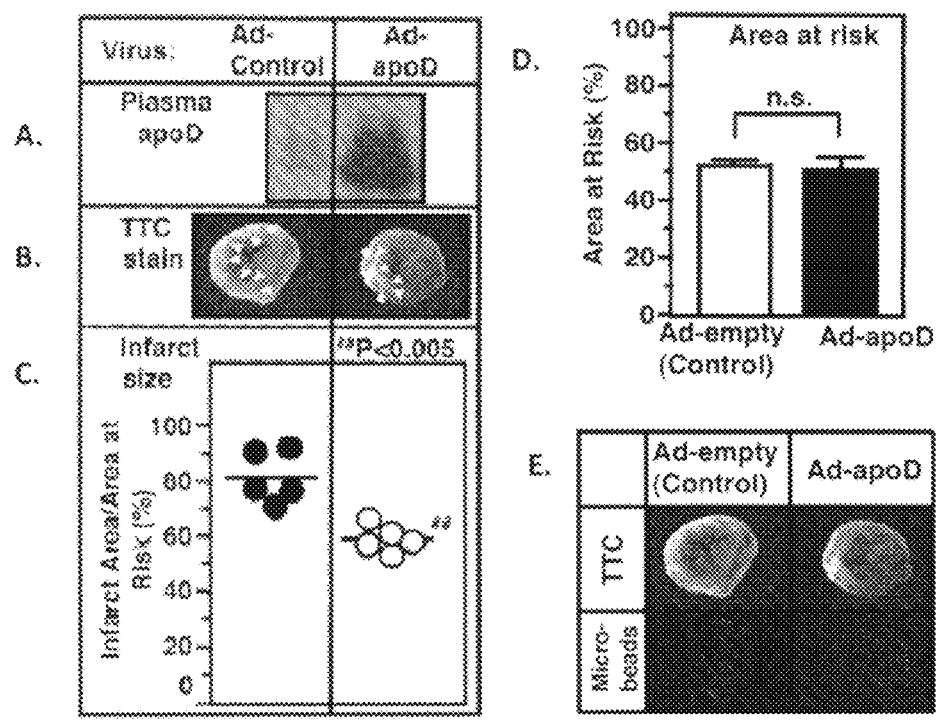
FIG. 3A is an immunoblot showing ApoD protein levels in plasma after adenovirus-mediated hepatic overexpression of ApoD. Male wild-type C57BL/6 mice (9 weeks old) were injected with adenoviruses encoding mouse ApoD (Ad-ApoD, n=5, right) or an 'empty vector' control (Ad-control, n=5, left). Four days later, the mice were subjected to myocardial ischemia (60 minutes)/reperfusion (24 hrs). SDS-PAGE/immunoblotting was performed using plasma proteins (30 µg protein/lane) four days after virus injection (prior to surgery).
FIG. 3B shows images of infarct size after in vivo myocardial ischemia reperfusion (I/R) injury in wild-type C57BL/6 mice. Representative images of 2,3,5-triphenyl tetrazolium chloride (TTC) stained sections of hearts from virus-injected mice are shown. Infarct areas (white) are indicated with arrow heads.
FIG. 3C depicts a graph quantifying relative infarct sizes (infarct area/AAR) in hearts from virus-injected mice in FIG. 3B ($^{\#\#\#}$P<0.005).
FIG. 3D depicts a graph showing the average area at risk of hearts from mice injected with either Ad-control (left) or Ad-ApoD (right) (n.s., differences were not statistically significant).
FIG. 3E shows representative images of TTC stained sections and fluorescent images of the same sections of hearts from Ad-control (left) or ApoD (right) injected mice. For FIGS. 3D and 3E, male wild-type C57BL/6 mice (9 weeks old) were injected via the tail vein with $2.5 \times 10^8$ PFU of adenoviruses encoding either mouse ApoD (Ad-ApoD, n=5) or an 'empty vector' control (Ad-control, n=5). Four days later, the mice were subjected to myocardial I/R injury by ligation of the left coronary artery with a snare (60 minute ischemia). Fluorescent microspheres were injected during this period of ischemia to visualize the area at risk (AAR). The ligation snare was released and 24 hours later (reperfusion period) the hearts were harvested and sectioned. The sections were stained with 2,3,5-triphenyl tetrazolium chloride (TTC) to visualize the infarct areas. The area at risk (the region free of fluorescent signal from the microspheres) for each heart was determined by analysis of images recorded using light and fluorescence microscopy.

ApoD Overexpression in the Liver Protects Against Heart Tissue Damage Induced by Myocardial Infarction A preliminary study was conducted to determine the levels of circulating ApoD upon injecting mice with an adenovirus encoding mouse ApoD (Ad-ApoD) or an empty vector control adenovirus (Ad-control). This study showed that levels of plasma ApoD protein detected by immunoblotting 4 days after injection were ~20-fold higher in the Ad-ApoD injected mice than in the Ad-control injected mice (FIG. 3A). The level of plasma ApoD in the Ad-control injected mice was similar to that in uninjected wild-type mice (not shown). Ischemia (60 min)/reperfusion (~24 h) procedure was conducted 4 days after injection of wild-type C57BL/6 mice with Ad-ApoD or Ad-control virus. At the end of the reperfusion period, the ventricles were excised and cut into 1 mm thick sections (typically, 5 sections/heart), stained with TTC, and fixed. Photomicrographs of the sections were used to quantitate the infarct area (white region, absence of stain) and the area at risk (tissue subjected to ischemia, see Methods). The areas at risk were similar for Ad-control and Ad-ApoD-treated mice (~50% of total heart) (FIGS. 3D and 3E). Images of representative sections with arrowheads indicating infarcts are shown in FIG. 3B and the ratios of infarct area-to-area at risk are shown in FIG. 3C. As shown in FIG. 3C, the Ad-ApoD induced increase in plasma ApoD levels significantly decreased the relative infarct size (59% vs 81%, P<0.005), suggesting increased plasma ApoD protected the hearts of wild-type mice.

Loss of ApoD Expression Exacerbates Heart Tissue Damage

Figure 4:
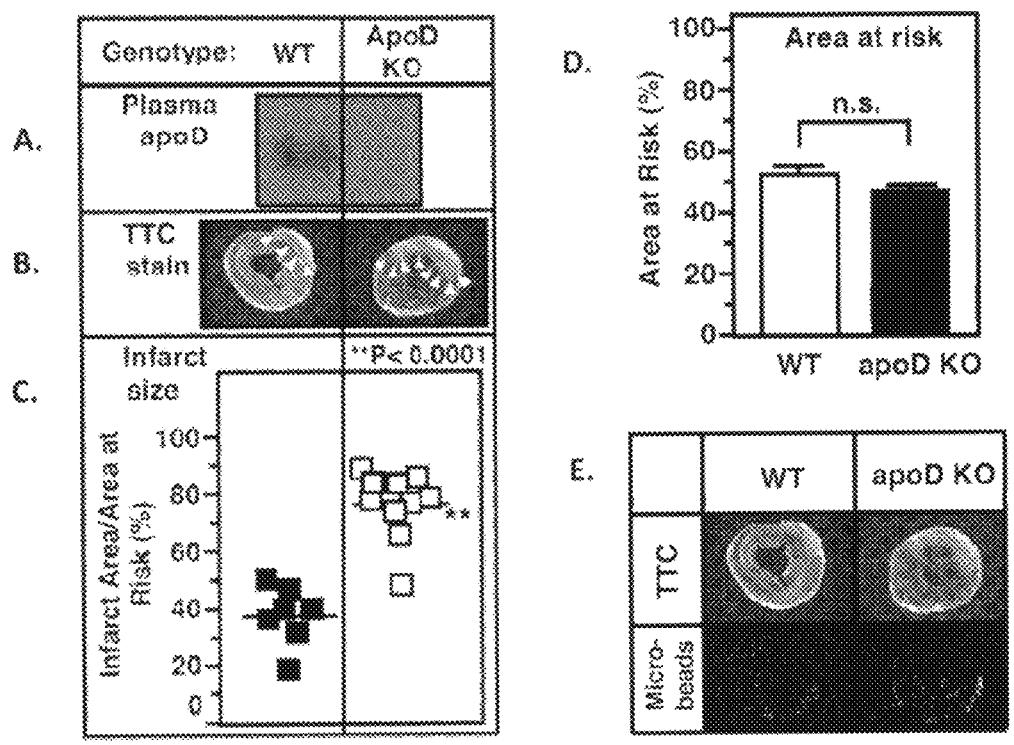
FIG. 4A depicts an immunoblot showing ApoD protein levels in plasma of homozygous ApoD null mice compared to wild type mice. Male wild-type (WT, n=7, left) or homozygous null ApoD KO (ApoD KO, n=10, right) mice on a C57BL/6 background (11 weeks old) were subjected to myocardial ischemia (45 minutes)/reperfusion (24 h).
FIG. 4B shows representative images of TTC stained sections of hearts.
FIG. 4C depicts a graph quantifying relative infarct sizes (infarct area/AAR) in hearts from dKO and wild type mice (**P<0.0001). Each square represents results from one animal and horizontal lines represent means.
FIG. 4D depicts a graph showing the average area at risk of hearts from WT (left) or ApoD KO (right) mice (n.s., differences were not statistically significant). Error bars represent SEM.
FIG. 4E shows representative images of TTC stained sections and fluorescent images of the same sections of hearts from WT (left) or ApoD KO (right) mice. For both FIGS. 4D and 4E, male wild-type (WT, n=7) or homozygous null ApoD KO (ApoD KO, n=10) mice on a C57BL/6 background (11 weeks old) were subjected to myocardial I/R injury by ligation of the left coronary artery with a snare (45 minute ischemia). Fluorescent microspheres were injected during this period of ischemia to visualize the area at risk (AAR). The ligation snare was released and 24 hours later (reperfusion period) the hearts were harvested and sectioned. The sections were stained with 2,3,5-triphenyl tetrazolium chloride (TTC) to visualize the infarct areas. The area at risk (the region free of fluorescent signal from the microspheres) for each heart was determined by analysis of images recorded using light and fluorescence microscopy.

FIG. 4 compares the results of the ischemia (45 min)/reperfusion (~24 h) procedure on wild-type (WT, left) and ApoD KO (ApoD KO, right) mice. Immunoblotting analysis showed no detectable ApoD in the plasma of ApoD KO mice (FIG. 4A). The areas at risk (~50% of total) were similar for WT and ApoD KO mice (FIGS. 4D and 4E). Loss of ApoD in the KO mice was associated with a significant increase in infarct area (76% for KO mice vs 37% for control mice, P<0.0001, FIGS. 4B and 4C). Taken together, the effects on cardiac ischemia/reperfusion injury of both the loss of expression and increased expression of ApoD suggest that ApoD is cardioprotective and that the increased ApoD expression in the hearts of dKO mice with increased CAD protect hearts against damage due to I/R.

Example 4

ApoD Protects Cardiomyocytes Against Hypoxia/Reoxygenation Stress

To address the mechanism of ApoD-mediated cardioprotection, the ability of exogenous ApoD protein to protect cardiomyocytes against hypoxia/reoxygenation (H/R) stress in vitro was examined. Primary adult rat ventricular myocytes (ARVMs) or neonatal rat ventricular myocytes (NRVMs) were cultured and subjected to H/R stress in the absence and presence of purified human ApoD added to the culture medium.

Figure 5:
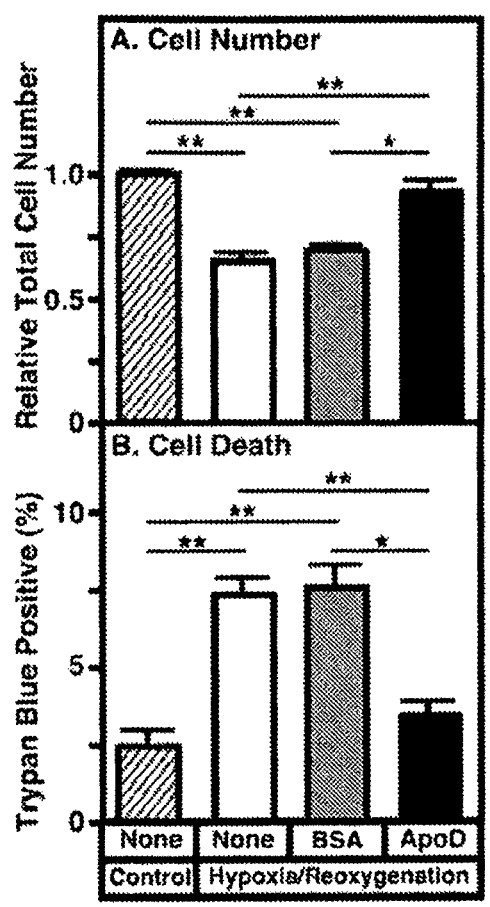
FIG. 5 is an analysis of the effects of human ApoD on hypoxia/reoxygenation (H/R) stress in cultured adult rat ventricular myocytes (ARVMs). ARVMs were plated onto laminin-coated P-35 cell culture dishes, and cultured in medium B overnight. The ARVMs were then pre-incubated for 1 hour in medium B without (n=9) or with 100 µg/mL of either human ApoD (n=9) or BSA (n=9) followed by 16 hours of anoxia (95% $N_2$ and 5% $CO_2$ atmosphere) in a modular incubator chamber (hypoxia). They were then incubated for 8 hours under normal conditions (21% oxygen) (reoxygenation). The ApoD or BSA was present as indicated throughout the H/R procedure. In addition, control ARVMs were incubated in a normal atmosphere throughout (n=8).

ARVMs were incubated in standard culture medium in the absence or presence of 100 μg/mL of either purified human ApoD or BSA as a control. The cells were subjected to hypoxia for 16 h (95% $N_2$/5% $CO_2$) followed by reoxygenation for 8 h (95% air/5% $CO_2$), after which total cell number and loss of cell membrane integrity (trypan blue positive cells) were evaluated. The concentration of ApoD added to the culture media was similar to that observed in human plasma (75-300 μg/mL, or approximately 3-12 μM). FIG. 5 shows that H/R stress significantly reduced total cell number (FIG. 5A, white bars, compare to hatched bars for control cells without additions) and increased the fraction of trypan blue positive staining cells (FIG. 5B). Treatment with ApoD significantly reversed these effects of H/R-induced cell damage (FIGS. 5A and 5B, black bars), whereas treatment with BSA did not significantly alter the consequences of H/R (gray bars). Treatment of control cells not subjected to H/R stress with either ApoD or BSA did not significantly influence total cell number or trypan blue staining (data not shown). These results suggest that ApoD protects cultured adult cardiomyocytes against FUR stress.

Figure 6:
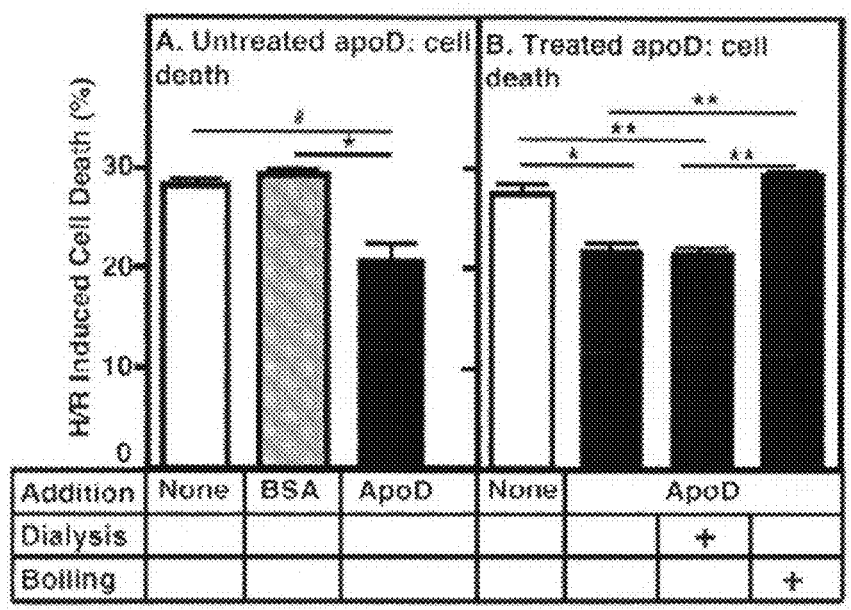
FIG. 6 is an analysis of the effects of untreated, dialyzed, or boiled ApoD on hypoxia/reoxygenation (FUR) stress in cultured neonatal rat ventricular myocytes (NRVMs). NRVMs isolated from 1 to 2 day old Wistar rats were plated onto 96 well plates and incubated for 48 hours prior to hypoxia/reoxygenation treatments in medium A. NRVMs (n=8 for each condition) were then pre-incubated for 1 hour in medium B or without or with 100 µg/mL of either untreated, extensively dialyzed or boiled (5 min) human ApoD or BSA followed by 24 hours of hypoxia (95% $N_2$ and 5% $CO_2$ atmosphere) in a modular incubator chamber (hypoxia). They were then incubated for 6 hours under a normal atmosphere (reoxygenation). ApoD or BSA were present as indicated throughout the H/R procedure. In addition, control NRVMs were incubated in a normal atmosphere throughout. At the end of reoxygenation period, the relative cell viability of each well was assessed using the CellTiter Blue reagent (Promega), and is presented as H/R induced cell death (% of cells).

These results were confirmed using NRVMs subjected to hypoxia (24 h)/reoxygenation (6 h). Cell viability was assessed using the CellTiter Blue reagent (Promega) in a 96-well format. FIG. 6A shows that treatment with 100 μg/mL ApoD, but not BSA, significantly reduced (p<0.001) H/R-induced cell death. Thus, ApoD protected NRVM as well as ARVM cells against H/R stress. The results in FIGS. 5 and 6 collectively suggest that cardioprotection conferred by ApoD in vivo may be a consequence of secreted ApoD directly sparing cardiomyocytes from ischemia/reperfusion injury.

Example 5

Mechanism of ApoD-Mediated Cardiomyocyte Protection

One potential mechanism by which ApoD protects cells from stress is that it carries a protective small molecule in its hydrophobic pocket that binds (Perdomo et al., *Aging* 2009; 1:17-27; Muffat et al., *Cell Cycle* 2010; 9:269-73; Eichinger et al., *JBC* 2007; 282:31068-75) ligands such as progesterone (Kd~0.4 μmol/L) and arachidonic acid (Kd~0.01 μmol/L) (Pearlman et al., *JBC* 1973; 248:5736-41; Dilley et al., *Breast Cancer Res Treat* 1990; 16:253-60; Morais et al., *FEBS Lett* 1995; 366:53-6). To determine if relatively weakly bound ligands of ApoD were responsible for its cardiomyocyte protective activity, human ApoD was extensively dialyzed and its activity examined in the H/R assay using NRVMs (CellTiter-blue assay). FIGS. 6A and B shows that extensive dialysis did not significantly reduce ApoD's activity, and thus, it is unlikely that a relatively weakly bound ligand is responsible for its activity. To assess the role of ApoD's conformation on its cardiomyocyte protective activity, ApoD was denatured by boiling (100° C., ≥5 min) prior to addition to NRVMs. FIG. 6B shows that boiling eliminated virtually all ApoD activity. These results suggest that the properly folded conformation of ApoD is essential for its cardiomyocyte protective activity.

Figure 7:
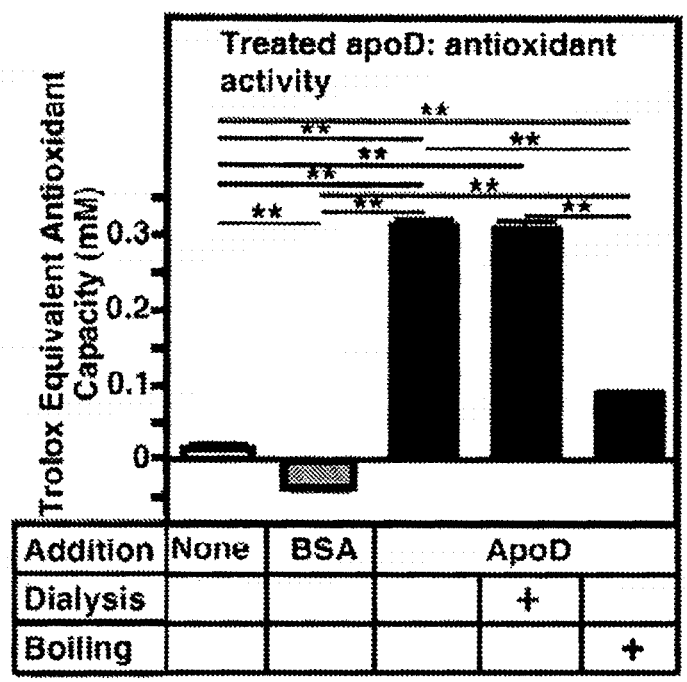
FIG. 7 depicts the effects of untreated, dialyzed or boiled ApoD on in vitro oxidation of ABTS. The in vitro antioxidant capacities of 30 µg/mL of either untreated, extensively dialyzed, or boiled (5 min) human ApoD or BSA were measured in the wells of 96 well plates using the ABTS chromogenic reaction for 45-60 minutes at room temperature (n=8 for each condition). Antioxidant capacity is presented as Trolox) equivalents. Error bars represent SEM. (#, P<0.001; *, P<0.0005; **, P<0.0001.)

The potential antioxidant activity of ApoD was tested in vitro using an assay in which the oxidation of the small molecule 2,2'-azino-bis(3-ethylbenzthiazoline-6-sulfonic acid) diammonium salt (ABTS) by hydroperoxide and myoglobin generates a colored product (Miller et al., *Free Radic Res* 1997; 26:195-9). The ability of ApoD to inhibit this reaction was compared with that of the control small molecule antioxidant Trolox (a water-soluble derivative of vitamin E). FIG. 7 shows that ApoD exhibited a very potent antioxidant activity—1.2 μmol/L ApoD was equivalent to 314 μmol/L Trolox. Extensive dialysis did not inhibit the antioxidant activity of ApoD in the ABTS assay, whereas boiling decreased its activity by 71% (FIG. 7). These results suggest that the proper folded conformation of ApoD, but not a relatively weakly bound ligand, is essential for the antioxidation activity of ApoD in this assay.

SUMMARY OF SEQUENCE IDENTIFIERS

| SEQ ID | Description | Sequence |
|---|---|---|
| 1 | Human mature ApoD (amino acid) | qafhlgkcpnppvqenfdvnkylgrwyeiekipttfengrciqanyslmengki kvlnqelradgtvnqiegeatpvnltepaklevkfswfmpsapywilatdyeny alvysctciiqlfhvdfawilarnpnlppetvdslkniltsnnidvkkmtvtdq vncpkls |
| 2 | Human mature ApoD (nucleic acid) | caagcatttcatcttgggaagtgccccaatcctccggtgcaggagaattttgac gtgaataagtatctcggaagatggtacgaaattgagaagatcccaacaacctt gagaatggacgctgcatccaggccaactactcactaatggaaaacggaaagatc aaagtgttaaaccaggagttgagagctgatggaactgtgaatcaaatcgaaggt gaagccacccagttaacctcacagagcctgccaagctggaagttaagttttcc tggtttatgccatcggcaccgtactggatcctggccaccgactatgagaactat gccctcgtgtattcctgtacctgcatcatccaactttttcacgtggattttgct tggatcttggcaagaaaccctaatctccctccagaaacagtggactctctaaaa aatatcctgacttctaataacattgatgtcaagaaaatgacggtcacagaccag gtgaactgccccaagctctcg |
| 3 | Human ApoD precursor (amino acid) | mvmlllllsalaglfgaaegqafhlgkcpnppvqenfdvnkylgrwyeiekipt tfengrciqanyslmengkikvlnqelradgtvnqiegeatpvnltepaklevk fswfmpsapywilatdyenyalvysctciiqlfhvdfawilarnpnlppetvds lkniltsnnidvkkmtvtdqvncpkls |
| 4 | Human ApoD precursor (nucleic acid) | atggtgatgctgctgctgctgctttccgcactggctggcctcttcggtgcggca gagggacaagcatttcatcttgggaagtgccccaatcctccggtgcaggagaat tttgacgtgaataagtatctcggaagatggtacgaaattgagaagatcccaaca acctttgagaatggacgctgcatccaggccaactactcactaatggaaaacgga aagatcaaagtgttaaaccaggagttgagagctgatggaactgtgaatcaaatc gaaggtgaagccacccagttaacctcacagagcctgccaagctggaagttaag ttttcctggtttatgccatcggcaccgtactggatcctggccaccgactatgag aactatgccctcgtgtattcctgtacctgcatcatccaactttttcacgtggat tttgcttggatcttggcaagaaaccctaatctccctccagaaacagtggactct ctaaaaaatatcctgacttctaataacattgatgtcaagaaaatgacggtcaca gaccaggtgaactgccccaagctctcg |

We claim:

1. A method of treating ischemic injury in a tissue of a subject or treating a subject at risk of tissue damage associated with ischemia, comprising administering to the subject a composition comprising an effective amount of purified, recombinant or chemically synthesized human ApoD, or an active variant thereof, wherein the active variant reduces ischemic damage to tissue and comprises an amino acid sequence having at least 90% identity to human ApoD comprising the amino acid sequence set forth in SEQ ID NO: 1, thereby treating ischemic injury in the tissue or treating the subject at risk of tissue damage.

2. The method of claim 1, wherein the active variant of human ApoD comprises an amino acid sequence having about 95% or about 99% identity to SEQ ID NO: 1.

3. The method of claim 1, wherein human ApoD comprises the amino acid sequence set forth in SEQ ID NO: 1.

4. The method of claim 1, wherein the active variant of ApoD comprises a chimeric polypeptide comprising human ApoD and a heterologous polypeptide that increases the circulating half-life of the chimeric polypeptide compared to wild-type human ApoD.

5. The method of claim 1, wherein the active variant of human ApoD is a fragment of human ApoD that reduces ischemic damage to tissue.

6. The method of claim 5, wherein the fragment comprises at least 160 amino acids of mature human ApoD.

7. The method of claim 1, wherein the active variant of human ApoD is a fragment of human ApoD that reduces death of cardiomyocytes.

8. The method of claim 1, wherein the active variant comprises an alanine substitution at amino acid 49, amino acid 157, or both amino acids 49 and 157 of human ApoD comprising the amino acid sequence set forth in SEQ ID NO: 1.

9. The method of claim 1, wherein the active variant comprises an aglycosylated variant comprising an amino acid substitution at Asn 45, Asn 78 or both amino acids Asn 45 and Asn 78 of human ApoD comprising the amino acid sequence set forth in SEQ ID NO: 1.

10. The method of claim 1, further comprising administering one or more additional therapeutic agents or treatments.

11. The method of claim 10, wherein the one or more therapeutic agents is selected from the group consisting of: angiotensin-converting enzyme (ACE) inhibitors (e.g., enalapril, lisinopril, and captopril), angiotensin II (A-II) receptor blockers (e.g., losartan and valsartan), diuretics (e.g., bumetanide, furosemide, and spironolactone), digoxin, beta blockers, nesiritide, cholestyramine, colestipol, nicotinic acid, gemfibrozil, probucol, atorvastatin, lovastatin, aspirin, ticlopidine, clopidogrel, anti-coagulants, inhibitors of smooth muscle proliferation, inhibitors of DP1 and/or DP2 receptor, inhibitors of MAP kinase, fibroblast growth factors (e.g., FGF1, FGF2, and FGF5), vascular endothelial growth factors (VEGF) and active fragments thereof (e.g., $VEGF_{165}$), hypoxia inducible factor (HIF-1), platelet-derived growth factors (PDGF1, PDGF2), developmental embryonic locus (DEL) 1, angiopoietins, hepatocyte growth factor (HGF), monocyte chemoattractant protein (MCP-1), endothelial nitric oxide synthase (eNOS), inducible nitric oxide synthase (iNOS).

12. The method of claim 10, wherein the one or more therapeutic treatments is selected from the group consisting of: angioplasty, single coronary artery bypass grafting (CABG), or multiple CABG.

13. The method of claim 1, wherein the tissue is selected from the group consisting of heart, brain, kidney, bowel, liver, skeletal muscle, and skin.

14. The method of claim 1, wherein the ischemic injury is associated with a disease or disorder selected from the group consisting of: coronary artery disease, myocardial infarction, stroke, peripheral arterial disease, peripheral vascular disease, and surgery involving temporary disruption of blood flow.

15. The method of claim 1, wherein the subject has one or more clinical indicators of coronary artery disease selected from the group consisting of frequency and intensity of anginal symptoms, myocardial perfusion, electrocardiogram tracings, scores on quantitative angina scales, and angiography.

16. The method of claim 1, wherein the area of tissue damage relative to the area at risk of damage is reduced up to about 90%, up to about 80%, up to about 70%, up to about 60%, up to about 50%, up to about 40%, up to about 30%, up to about 20%, up to about 10%, or up to about 5%.

17. The method of claim 1, wherein the composition is administered directly to damaged tissue or tissue at risk of damage by ischemia.

18. The method of claim 1, wherein the composition is administered to a tissue other than damaged tissue or tissue at risk of damage by ischemia.

19. The method of claim 1, wherein the composition is administered by a route selected from the group consisting of oral, intravenous injection, subcutaneous injection, intramuscular injection, myocardial injection, intrapericardial injection, endomyocardial injection, or intracoronary infusion.

20. A method of increasing the amount of circulating ApoD, or an active variant thereof in a subject in need thereof, comprising administering to the subject a composition comprising purified, recombinant or chemically synthesized human ApoD, or active variant thereof, wherein the active variant reduces ischemic damage to tissue and comprises an amino acid sequence having at least 90% identity to human ApoD comprising the amino acid sequence set forth in SEQ ID NO: 1, wherein an increase in the amount of circulating ApoD reduces tissue damage in the subject.

21. A method of treating tissue damage associated with coronary artery disease in a subject or treating a subject at risk of tissue damage associated with coronary artery disease, comprising administering to the subject a composition comprising an effective amount of purified, recombinant or chemically synthesized ApoD, or an active variant thereof, wherein the active variant reduces ischemic damage to tissue and comprises an amino acid sequence having at least 90% identity to human ApoD comprising the amino acid sequence set forth in SEQ ID NO: 1, thereby treating tissue damage in the subject or treating the subject at risk of the tissue damage.

* * * * *